United States Patent [19]
Paszczynski et al.

[11] Patent Number: 5,486,214
[45] Date of Patent: Jan. 23, 1996

[54] BIODEGRADABLE AZO DYES

[75] Inventors: Andrzej Paszczynski; Stefan Goszczynski; Ronald L. Crawford; Donald L. Crawford; Maria B. Pasti, all of Moscow, Id.

[73] Assignee: Idaho Research Foundation, Inc., Moscow, Id.

[21] Appl. No.: 930,162

[22] Filed: Aug. 12, 1992

Related U.S. Application Data

[63] Continuation-in-part of Ser. No. 675,514, Mar. 27, 1991.
[51] Int. Cl.$^6$ .................................................. C09B 67/02
[52] U.S. Cl. .................. 8/524; 8/525; 8/641; 435/189; 435/166; 435/254.1; 435/190; 534/845
[58] Field of Search .............................. 8/524, 525, 641; 435/189, 166, 254, 190, 191; 534/845

[56] References Cited

U.S. PATENT DOCUMENTS

| | | | |
|---|---|---|---|
| 313,118 | 3/1885 | Stebbins, Jr. | 534/845 X |
| 2,788,344 | 4/1957 | Brassel . | |
| 2,977,353 | 3/1961 | Stephen | 8/524 |
| 3,297,679 | 1/1967 | Leuchs . | |
| 3,342,804 | 9/1967 | Mueller | 8/524 |
| 3,676,050 | 7/1972 | James | 8/41 |
| 3,905,952 | 9/1975 | Speck | 534/845 X |
| 3,932,376 | 1/1976 | Feeman | 534/845 X |
| 4,249,902 | 2/1981 | Kruchenberg et al. | 8/525 |
| 4,445,905 | 5/1984 | Schaetzer et al. | 8/641 |
| 4,539,009 | 9/1985 | Nickel et al. | 8/641 |
| 4,687,741 | 8/1987 | Farrell et al. | 435/189 |
| 4,749,784 | 6/1988 | Feeman et al. | 8/641 |
| 5,036,013 | 7/1991 | Wood et al. | 435/281 |
| 5,141,855 | 8/1992 | Schmittou . | |
| 5,153,121 | 10/1992 | Asther et al. | 435/71.1 |

FOREIGN PATENT DOCUMENTS

| | | |
|---|---|---|
| 2110614 | 3/1970 | Germany . |
| 48-75926 | 10/1973 | Japan . |
| 1562991 | 3/1980 | United Kingdom . |

OTHER PUBLICATIONS

CAS Registry Handbook, pp. 1126R and 2766R (1974).
Colour Index, 3rd, ed., vol. 4, pp. 4043 and 4087 (1971).
Aspro–Nicholas, Chem. Abstracts, vol. 66, No. 75812n (1967).
Gholse et al., Chem. Abstracts, vol. 86, No. 33764f (1971).
Jain et al., Chem. Abstracts, vol. 81, No. 38911h (1974).
Yoshida et al. I, Chem. Lett., vol. 5 pp. 703–706 (1988).
"Interference of Aromatic Sulfo Groups in the Microbial Degradation of the Azo Dyes Orange I and Orange II" *Arch. of Microbiol.*, 35:1–7 (1983).
"Biodegradation of Azo & Heterocyclic Dyes by *Phanerochaete chrysosporium*" *Applied and Environmental Microbiology*, pp. 1114–1118, vol. 6, No. 4 (1990).
H. G. Kulla's "Experimental Evolution of Azo Dye–Degrading Bacteria," *Curr. Perspect. Microb. Ecol., Proc. Int. Symp.* 3rd, 663–667 (1984).
Haraguchi's "Degradation of Ligin–Related Polystryene Derivatives by Soil Microflora and *Micromonospora*–SP Yb–1" vol. 2 (1980).
Haraguchi's "Biodegradation of Ligin–Related Polystyrenes" vol. 2 (1980).

(List continued on next page.)

*Primary Examiner*—Paul Lieberman
*Assistant Examiner*—Necholus Ogden
*Attorney, Agent, or Firm*—Klarquist Sparkman Campbell Leigh & Whinston

[57] ABSTRACT

A biodegradable azo dye contains a nitrogen atom linked to an aromatic ring having a lignin-like substitution pattern. The ring is preferably a syringyl or guaiacol moiety, and provides a naturally-occurring structure for attack by microorganisms, such as Streptomyces or Phanerochaete. In especially preferred embodiments, the aromatic ring has a first substituent $R_1$ selected from among hydroxy, lower alkoxy, or amino, and a second substituent $R_2$ selected from among lower alkyl, lower alkoxy and halogen. Some embodiments include a third ring substituent $R_3$ selected from the group lower alkyl, lower alkoxy, and halogen.

16 Claims, 9 Drawing Sheets

OTHER PUBLICATIONS

Brown's "Degradation of Dyestuffs: Part III–Investigations of the Ultimate Degradability" *Chemosphere*, vol. 16, No. 7 pp. 1539–1553 (1987).

Kulla's "Aerobic Bacterial Degradation of Azo Dyes" in *Microbiol Degradation of Xenobiotics and Recalcitrant Compounds*, Academic Press, London, pp. 387–399 (1981).

Brown's "The Aerobic Biodegradability of Primary Aromatic Amines," *Chemosphere*, vol. 12, No. 3, pp. 405–414 (1983).

Cerniglia's "Azoreductase Activity of Anaerobic Bacteria Isolated from Human Intestinal Microflora," *Applied and Environmental Microbiology*, vol. 56, No. 7, pp. 2146–2151 (1990).

Mason's "Inhibiton of Azoreductase by Oxygen" *Molecular Pharmacology*, 14, pp. 665–671 (1978).

Ogawa's "Biodegradation of Azo Dyes in Multistage Rotating Biological Contractor Immobilizd by Assimilating Bacteria," *Bull. Environ. Contam. Toxicol.*, 44:561–566 (1990).

Sandermann's "Mineralization of Chloraniline/Lignin Conjugates and of Free Chloroanailines by the White Rot Fungus *Phanerochaete chrysosporium*," *J. Agric. Food Chem.*, vol. 33, pp. 1055–1060 (1985).

Pasczcynski's "New Approach to Improve Degradation of Recalcitrant Azo Dyes by Streptomyces spp. and *Phaneerochaete chrysosporium*," *Enzyme Microb, Technol.*, vol. 13, pp. 1–7 (1991).

Zimmerman's *Eur. J. Biochem*, 129:197–203 (1982).

Wuhrman's *Eur J. Appl. Microbiol–Biotechnol*, 9:325–338 (1980).

Haider's *Soil Biol. Biochem*, 20:425–449 (1988).

Index Chemicus, vol. 29, 95988 (1968).

Cappadona et al., Chemical Abstracts, vol. 86, No. 33764f (1977).

Matusiak et al., Chemical Abstracts, vol. 86, No. 21734h (1977).

Yoshida et al. I, Chem. Lett., vol. 5, pp. 703–706 (1984).

Yoshida, et al. iI, J. Phys. Chem., vol. 94, pp. 4254–4259 (1990).

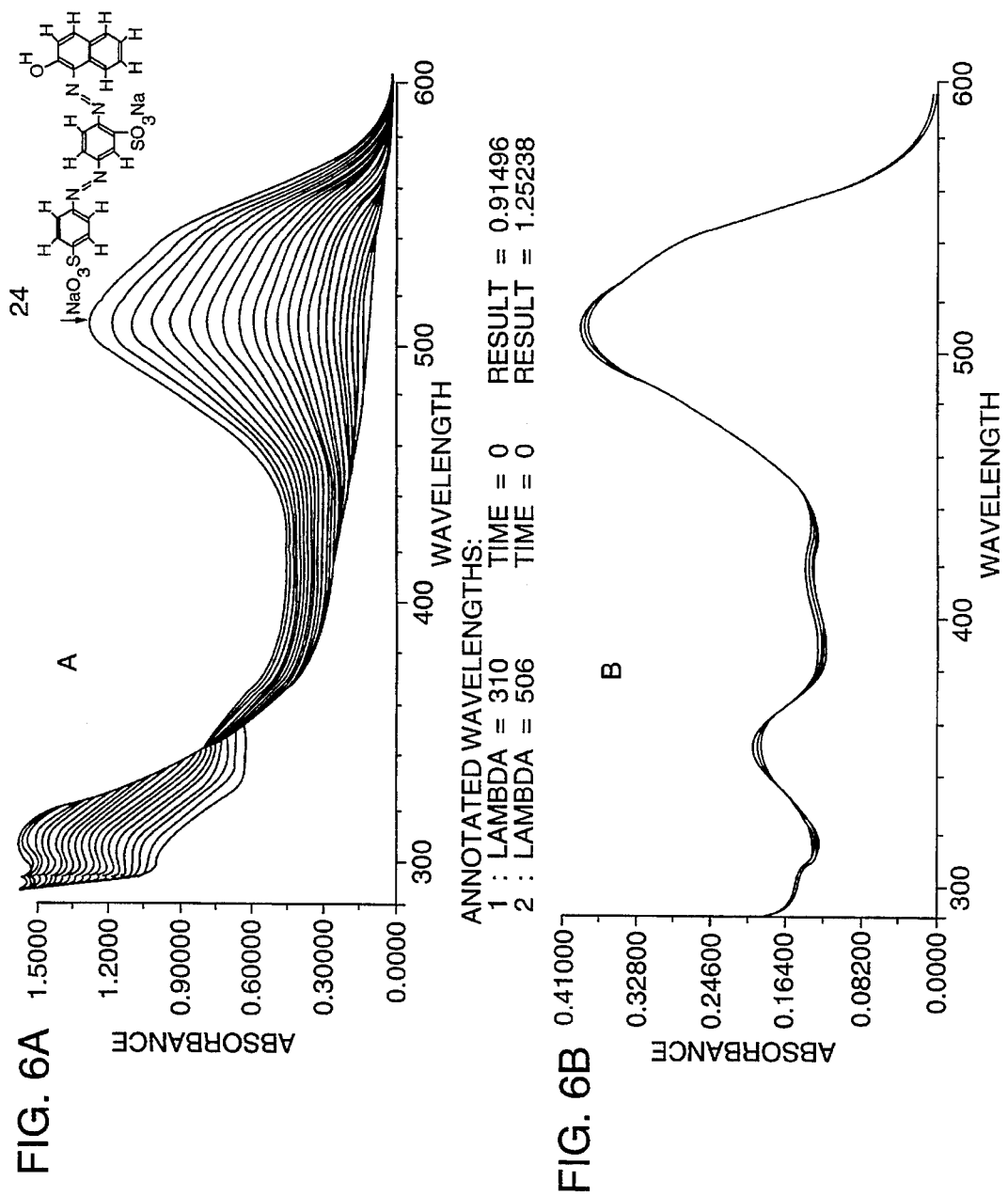

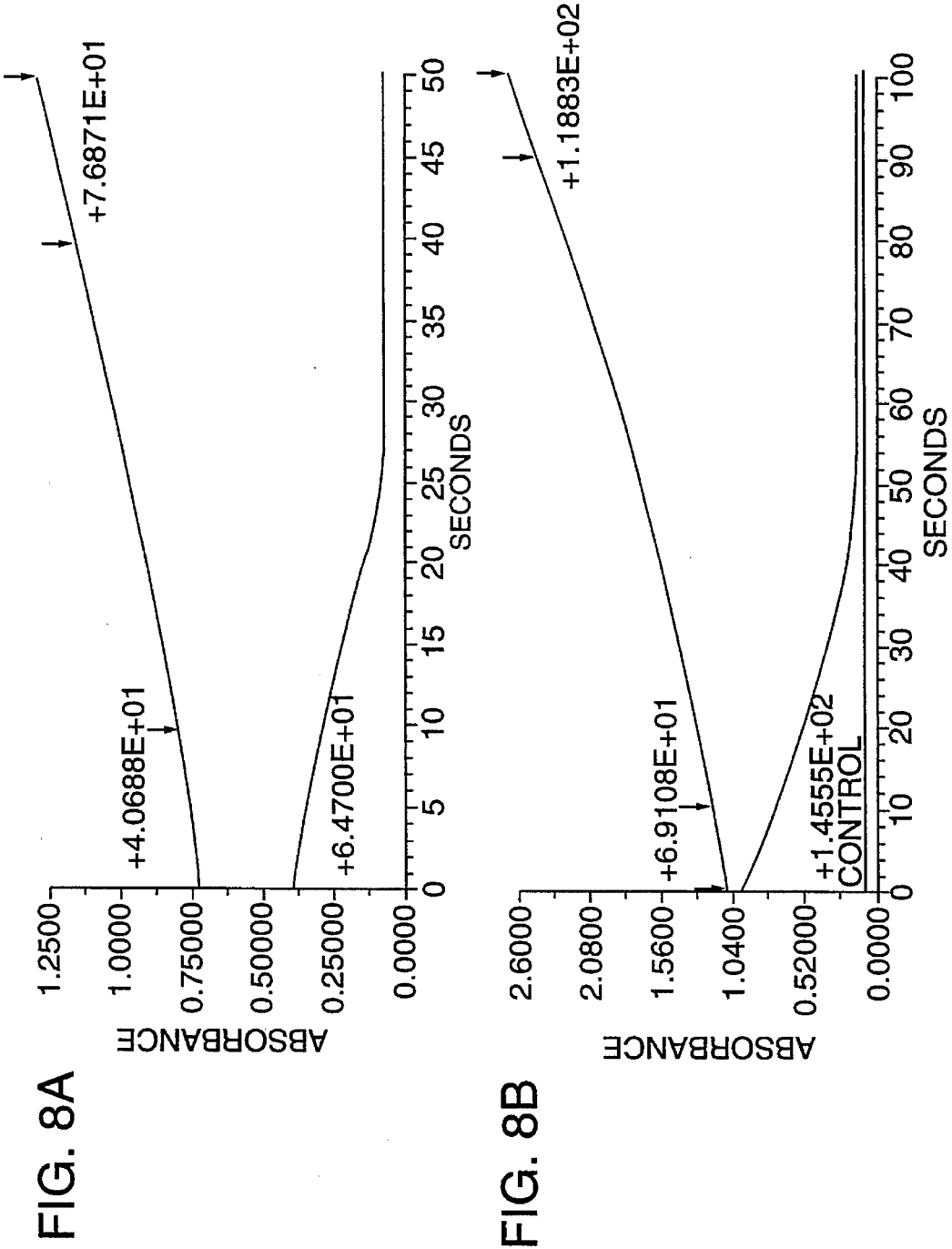

BIODEGRADABLE AZO DYES

GOVERNMENTAL SUPPORT

This research was supported by the Idaho Agricultural Experiment Station, by Competitive Research grant 88-37233-4037 from the United States Department of Agriculture, and by grant BCS-8807000 from the National Science Foundation. The government may have certain rights in this invention.

CROSS REFERENCE TO RELATED APPLICATION

This application is a continuation-in-part of U.S. patent application, Ser. No. 07/675,514, filed Mar. 27, 1991, entitled Biodegradable Azo Dyes. The disclosure of this parent application is incorporated herein by reference.

BACKGROUND OF THE INVENTION

1. Field of the Invention

This invention concerns a method of making xenobiotic compounds more biodegradable. More specifically, it concerns biodegradable azo dyes.

2. General Discussion of the Background

Azo dyes are important synthetic compounds that are widely used in the dyestuff and textile industries. Unfortunately, they are not biodegradable and tend to persist in the environment unless subjected to costly physical-chemical decontamination processes. Compounds such as azo dyes which resist biodegradation are known as xenobiotics. The azo linkages or aromatic sulfo groups often found in these dyes are generally not synthesized by living organisms, which may help explain their recalcitrance to degradation. Detailed knowledge about biodegradation of these compounds in nature is limited.

Biologic waste treatment processes are sometimes more efficient and less expensive than physical-chemical waste treatment procedures, hence it would be desirable to provide a biological process using microorganisms that degrade xenobiotic azo dyes. Unfortunately, efforts to isolate such microorganisms have been largely unsuccessful in producing a commercially suitable process. Azo dye degrading Pseudomonas strains have been isolated from chemostat cultures by Kulla, "Aerobic bacterial degradation of azo dyes", in *Microbial Degradation of Xenobiotic and Recalcitrant Compounds*, Academic Press, Inc., London, 1981, pages 387–399 (1981). The degradation mechanism described for that Pseudomonas involved an oxygen-insensitive azoreductase which catalyzed the reductive cleavage of the azo group using NAD(P)H as an electron donor. Zimmerman, et al., *Eur. J. Biochem.*, 1982, 129:197–203. Various anaerobic bacteria that degrade azo dyes have also been reported by Wuhrman, et al., *Eur. J. Appl. Microbiol. Biotechnol.*, 1980, 9:325–338 and Meyer, "Biodegradation of synthetic organic colorants", in *Microbial Degradation of Xenobiotic and Recalcitrant Compounds*, supra. However, under aerobic conditions these dyes have been considered to be essentially non-biodegradable.

More recently, however, Cripps found that the fungus *Phanerochaete chrysosporium* aerobically degrades polycyclic hydrocarbons containing azo and sulfo groups. Cripps, et al., *Appl. Environ. Microbiol.*, 1990, 56:1114–1118. That paper described several unidentified metabolites of microbially degraded Tropaeolin O, Congo Red and Orange II after incubation with crude ligninase preparations, but the possible mechanism of degradation was not explained. Other investigators have shown that *P. chrysosporium* can mineralize chloroaniline/lignin conjugates and xenobiotic molecules bound to humic acids. Haider and Martin, *Soil Biol. Biochem.*, 1988, 20:425–249.

In spite of these advances, the degree of microbial degradation of many azo dyes has remained low. Kulla's azo dye degrading Pseudomonas is highly substrate specific, and requires extensive screening procedures to isolate biodegradative strains. The extreme specificity of Kulla's bacterial strains decreases their practical use in industry because industrial effluents contain mixtures of dyes. Kulla, et al., "Biodegradation of xenobiotics; experimental evolution of azo dye-degrading bacteria", in *Current Perspectives in Microbial Ecology*, (eds. M. J. Klug and C. A. Reddy), American Society for Microbiology, Washington, D.C., pages 663–667. Moreover, the Pseudomonal strains completely and irreversibly lose their biodegradative ability when grown with the specific substrate for ten generations, as disclosed at page 664 of that publication. Finally, sulfonated aromatic groups in the substrate dyes disturbed the microbial degradative pathways and limited the usefulness of these microorganisms in degrading the vast quantities of industrially produced azo dyes.

Accordingly, it is an object of this invention to provide azo dyes which are more completely biodegradable.

Another object of the invention is to provide such dyes which can be degraded more effectively and discarded less expensively than many previous azo dyes.

Yet another object of the invention is to provide such dyes which are less harmful to the environment.

Another object of this invention is to provide azo dyes which can be degraded by microorganisms with less substrate specificity.

Another object is to provide such dyes which are degraded by relatively common and genetically stable microorganisms that better retain their biodegradative capacity through successive generations.

Finally it is an object of the invention to provide an improved method of treating azo dyes in which sulfonated azo compounds can be degraded.

These and other objects of the invention will be understood more clearly by reference to the following detailed description.

SUMMARY OF THE INVENTION

A biodegradable dye compound is disclosed which contains an azo group having a nitrogen atom linked to an aromatic ring in which the aromatic ring has a lignin-like substitution pattern that enhances biodegradability of the dye compound. In preferred embodiments, the aromatic ring has a substitution pattern that resembles a syringyl or guaiacyl moiety. In especially preferred embodiments, the ring has a first substituent $R_1$ selected from the group consisting of hydroxy, lower alkoxy, or amino, particularly secondary amine. In other embodiments, the ring further includes a second substituent $R_2$ selected from the group consisting of hydrogen, alkyl, lower alkoxy and halogen. In yet other preferred embodiments, the ring includes a third substituent $R_3$ selected from the group consisting of lower alkyl, lower alkoxy and halogen. In especially preferred embodiments $R_1$ is para to the azo linkage. In other preferred embodiments $R_2$ is ortho to $R_1$. In especially preferred embodiments $R_1$ is para to the azo linkage and $R_2$ is ortho to $R_1$.

These and other compounds can be included in a biodegradable composition in which the azo dye of the present invention is combined with an environmentally common microbe that is capable of degrading the azo dye. A wide variety of microorganisms efficiently degrade these dyes, especially microorganisms in the soil microflora. Particularly useful are a wide variety of Streptomyces species and strains of specific Streptomyces species found in soil and elsewhere. Examples of two aerobic microorganisms which have been shown to degrade the dyes of the present invention are several soil Streptomyces species and *Phanerochaete chrysosporium*. When used in combination with Streptomyces, biodegradation is most enhanced in the disclosed embodiments when $R_1$ is a hydroxy group para to the azo linkage, particularly if $R_2$ is ortho to the hydroxy.

Biodegradation with Phanerochaete is particularly enhanced in some embodiments wherein $R_1$ is hydroxy para to the azo linkage and $R_3$ is absent, especially if $R_2$ is a group that does not have a high degree of sterric hindrance. Methyl, methoxy and halogen are examples of small groups with a low sterric hindrance. The presence of $R_3$, however, can greatly enhance biodegradation in some embodiments wherein $R_1$ is a hydroxy group para to the azo linkage, and $R_2$ and $R_3$ are both ortho to $R_1$. This enhanced biodegradation is observed with $R_3$ present even in embodiments wherein $R_1$ is not para to the azo linkage.

In other embodiments of the invention, a preexisting azo dye can be modified after use but before disposal to render it more biodegradable by these organisms.

BRIEF DESCRIPTION OF THE DRAWINGS

FIG. 6A shows the oxidation of veratryl alcohol and azo dye 24 by lignin peroxidase.

FIG. 6B shows the oxidation of azo dye 24 by lignin peroxidase in the absence of veratryl alcohol.

FIG. 8A shows the oxidation rate of veratryl alcohol and azo dye 24 by ligninase.

FIG. 8B shows the oxidation rate of veratryl alcohol and azo dye 28 by ligninase.

DETAILED DESCRIPTION OF PREFERRED EMBODIMENTS

Three azo dyes were tested as substrates for degradation by twelve Streptomyces species and the white rot fungus *Phanerochaete chrysosporium*. The three azo dyes were the commercially available acid yellow 9 (4 -amino-1,1'-azobenzene-3,4'-disulfonic acid), and two synthesized dyes. The two synthesized dyes were azo dye 1 [4-(3-methoxy-4-hydroxyphenylazo)-azobenzene-3,4'-disulfonic acid] and azo dye 2 (3-methoxy-4-hydroxy-azobenzene- 4'-sulfonic acid). Sulfanilic acid and vanillic acid were also tested as substrates for degradation by the twelve Streptomyces species and the white-rot fungus *Phanerochaete chrysosporium*. None of the Streptomyces species degraded acid yellow 9 or sulfanilic acid. The linkage of a guaiacol molecule onto acid yellow 9 or sulfanilic acid via azolinkages resulted in dyes that were decolorized by five of the twelve Streptomyces strains. These Streptomyces were those that could also attack vanillic acid, which has the same ring substitution pattern (4-hydroxy-3-methoxy) as guaiacol. While *P.chrysosporium* transformed both acid yellow 9 and sulfanilic acid, the two guaiacol-substituted azo dyes were decolorized more readily by *P.chrysosporium* than the corresponding unsubstituted molecules. Ligninase and manganese peroxidase preparations from the *P. chrysosporium* culture were apparently involved in the degradation.

Source of Materials

Figure 1A:
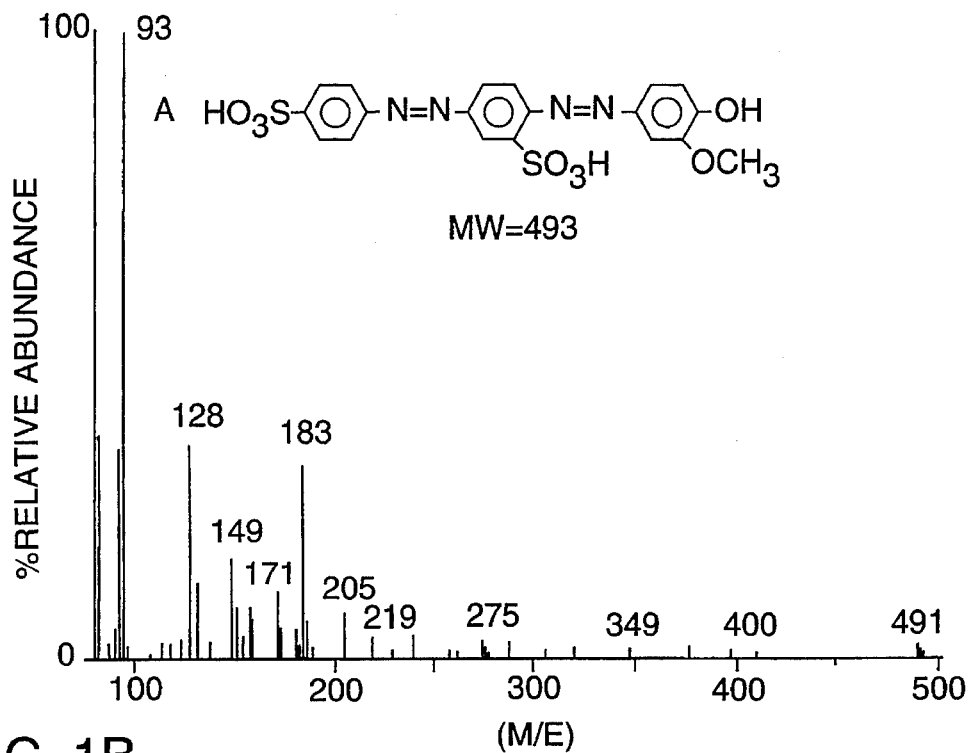
FIG. 1A shows the structure and MS spectra of the azo compound 4-(3-methoxy-4-hydroxyphenylazo)-azobenzene-3,4'-disulfonic acid of the present invention.
Figure 1B:
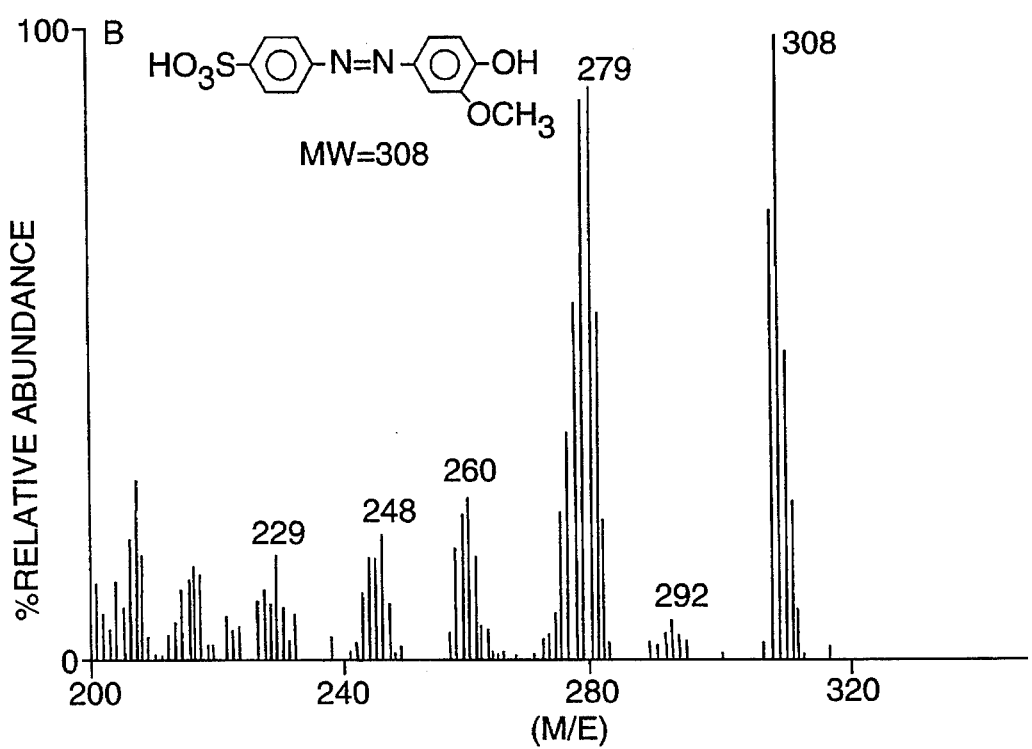
FIG. 1B shows the structure and MS spectra of the azo compound 3-methoxy-4-hydroxy-azobenzene-4'-sulfonic acid of the present invention.

Sulfanilic acid, guaiacol, sodium nitrite and 4 -hydroxy-3-methoxybenzoic acid (vanillic acid) were purchased from the Aldrich Chemical Co. The azo dye 4 -amino-1,1'-azobenzene-3,4'-disulfonic acid (acid yellow 9) was purchased from Sigma Chemical Co. Two additional azo dyes were synthesized by attaching guaiacol through an azo linkage to acid yellow 9, forming 4-(3-methoxy-4 -hydroxyphenylazo)-azobenzene-3,4'-disulfonic acid (azo dye 1), or to sulfanilic acid, forming 3-methoxy-4-hydroxy-azobenzene- 4'-sulfonic acid (azo dye 2). Structures and MS fragmentations of the dyes are shown in FIGS. 1a 1b. Purity of both synthesized dyes was determined by TLC and HPLC analysis; no significant impurities were detected. The HPLC integration data showed the purity was approximately 98% for azo dye 1 and 97% for azo dye 2.

Synthesis of Azo Dye 1

4-(3-methoxy-4-hydroxyphenylazo)-azobenzene-3,4'-disulfonic acid

Azo dye 1 was synthesized by dissolving 4-Amino-azobenzene- 3,4'-disulfonic acid sodium salt (0.76 g) in 5% sodium hydroxide (8 ml), and a solution of sodium nitrite (0.14 g in 0.5 ml of water) was added. Crushed ice (10 g) and concentrated HCl (1.8 ml) was introduced to the solution, which was then vigorously stirred for 15 minutes. To the cooled guaiacol solution (0.25 g dissolved in 3.2 ml 5% sodium hydroxide) the diazotised yellow 9 solution was added portionwise over 15 minutes with mechanical stirring. Saturated sodium chloride solution was added (15 ml), and the mixture was left to crystallize overnight at 5° C. The crystalline product was filtered, washed with acetone and ether, and dried in air. Dark brown crystals (0.98 g) were collected. (86.6% of theoretical yield).

The chemical structure of azo dye 1,4-(3-methoxy-4-hydroxyphenylazo)-azobenzene-3,4'-disulfonic acid, is:

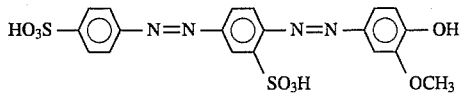

as supported by the MS spectra shown in FIG. 1A.

Synthesis of Azo Dye 2

3-methoxy-4-hydroxy-azobenzene-4'-sulfonic acid

Azo dye 2 was synthesized by suspending sulfanilic acid (1.73 g) in 23 ml of water, and 8 ml of 5% NaOH were added. The mixture was stirred until the acid dissolved and then sodium nitrite solution (0.7 g in 2 ml $H_2O$) was added. The solution was poured on a crushed ice (25 g) and concentrated HCL (2 ml) mixture and mixed until copious pecipitation took place (KJ starch test was positive). The diazotized sulfanilic acid was added portionwise to the cooled guaiacol solution (1.24 g in 20 ml 5% sodium hydroxide) with stirring. NaCl (20 g) was added and stirring was continued for 30 minutes at room temperature. The crystalline deep orange precipitate was filtered off and washed with ethanol and ether; 2.62 g of the product was obtained (64.4%) of theoretical yield).

The chemical structure of azo dye 2,3-methoxy-4-hydroxy-azobenzene-4'-sulfonic acid, is:

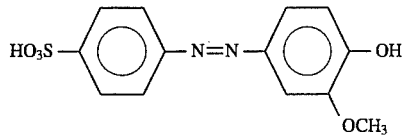

as supported by the MS spectra shown in FIG. 1B.

Azo Dyes 3–19

Analogous methods of synthesis were used to prepare azo dyes 3–19. The structures of these compounds are shown below.

Azo Dye 3
3,5-dimethyl-4-hydroxy-azobenzene-4'-sulfonic acid

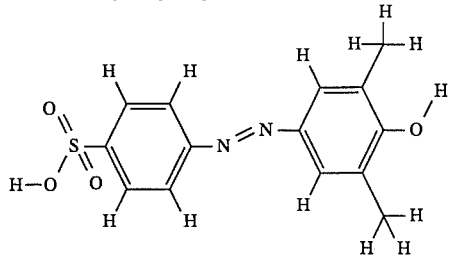

Azo Dye 4
3,5-dimethoxy-4-hydroxy-azobenzene-4'-sulfonic acid

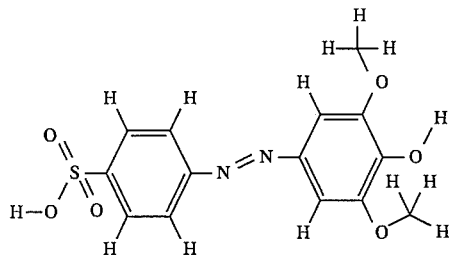

Azo Dye 5
3-methyl-4-hydroxy-azobenzene-4'-sulfonic acid

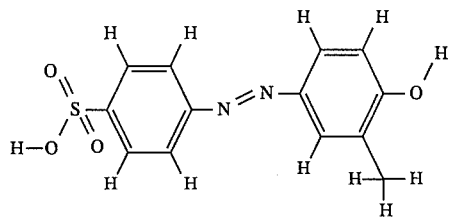

Azo Dye 6
4-hydroxy-azobenzene-4'-sulfonic acid

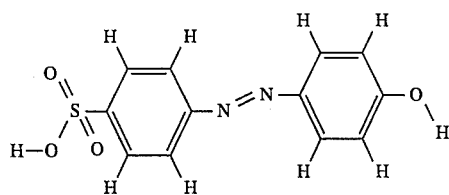

Azo Dye 7
2-hydroxy-4,5-dimethyl-azobenzene-4'-sulfonic acid

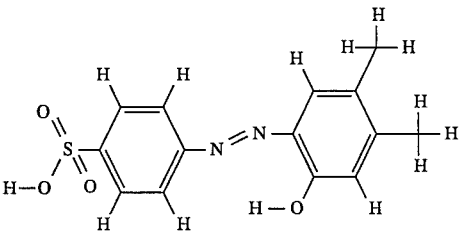

Azo Dye 8
2-hydroxy-5-methyl-azobenzene-4'-sulfonic acid

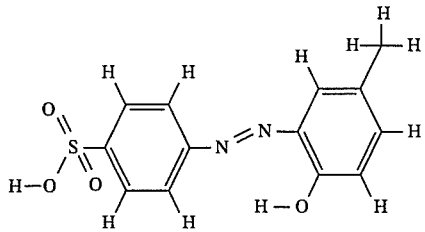

7
-continued

Azo Dye 9
2-hydroxy-5-ethyl-azobenzene-4'-sulfonic acid

Azo Dye 10
3-sec-butyl-4-hydroxy-azobenzene-4'-sulfonic acid

Azo Dye 11
2-hydroxy-3-methoxy-5-methyl-azobenzene-4'-sulfonic acid

Azo Dye 12
3,5-difluoro-4-hydroxy-azobenzene-4'-sulfonic acid

Azo Dye 13
3-chloro-4-hydroxy-azobenzene-4'-sulfonic acid

Azo Dye 14
4-dimethylamino-azobenzene-4'-sulfonic acid

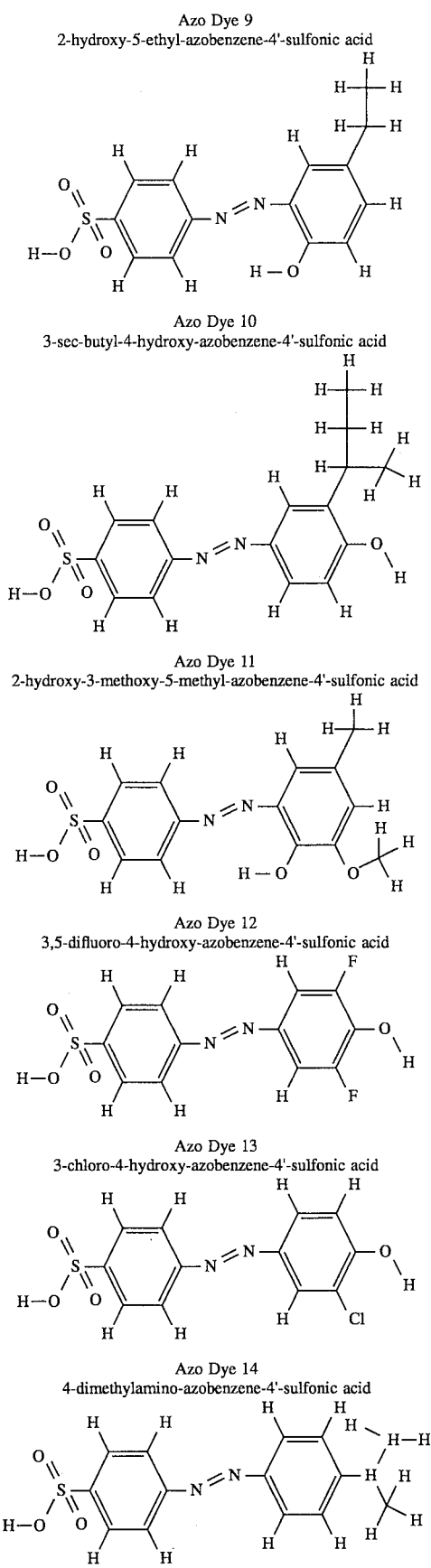

8
-continued

Azo Dye 15
4-diethylamino-azobenzene-4'-sulfonic acid

Azo Dye 16
4-methoxy-azobenzene-4'-sulfonic acid

Azo Dye 17
3,4-dimethoxy-azobenzene-4'-sulfonic acid

Azo Dye 18

Azo Dye 19

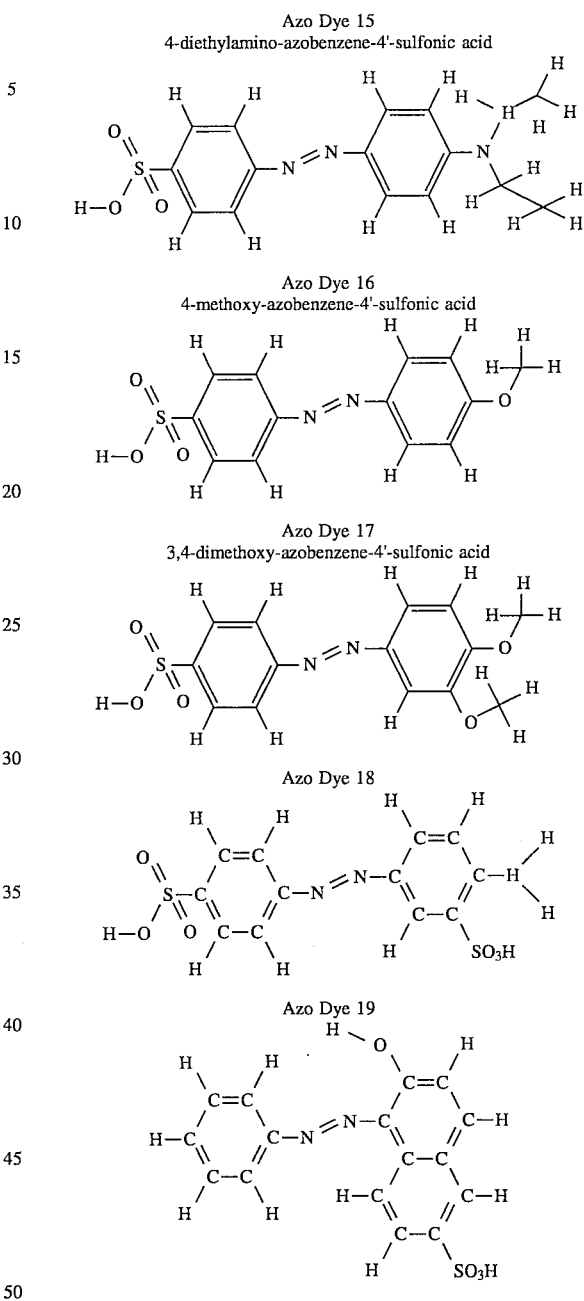

Microorganisms and Culture Maintenance

Twelve wild-type actinomycetes were selected from 20 strains isolated from higher termites in Kenya. Pasti and Belli, *FEMS Microbiol. Lett.*, 1985, 26:107–112. All strains have been identified as Streptomyces, based on the key of Williams, et al. *J. Gen. Microbiol.*, 1983, 129:1815–1830. Streptomyces viridosporus T7A (ATCC 39115) was isolated from soil by D. L. Sinden (M.S. thesis, University of Idaho, Moscow, 1979). Streptomyces badius 252 (ATCC 39117) was isolated from soil by Phelan et al. (*Can. J. Microbial,* 1979, 27:636–368) and Streptomyces SR-10 is a protoplast fusion recombinant derived from a cross between *S.viridosporus* T7A and *S.setonii* 75Vi2. Pette and Crawford, *Appl. Environ. Microbiol.*, 1984, 47:439–440. Stock cultures of the Kenyan isolates were maintained at 4° C. after growth and sporulation at 37° C. on the following medium in grams per liter of deionized water: $NH_4NO_3$, 1; $KH_2PO_4$, 0.4; yeast nitrogen base (Difco), 0.67; yeast extract (Difco), 0.2; lactose, 15; bacto-agar (Difco), 18. *S.viridosporus* T7A, *S.badius* 252 and S. SR-10 were maintained at 4° C. after growth and sporulation at 37° C. on yeast extract-malt extract dextrose agar, as in Pridham and Gottlieb, *J. Bacteriol.*, 1948, 56:107–114. Stock cultures were subcultered every 2 to 10 weeks, and distilled water suspensions of sporulated growth were used as initial inocula in all experiments.

*Phanerochaete chrysosporium* BKM-F-1767 (ATCC 24725) was obtained from The Forest Products Laboratory, Madison, Wis. The fungus was maintained and spore inocula were prepared as previously described by Huynh and Crawford, *FFMS Microbiol. Lett.*, 1985, 28:119–123.

All publications describing isolation of the Streptomyces and Phanerochaete, and all publications describing culture maintenance, are incorporated by reference.

Culture Conditions

Each Streptomyces species was grown in a cotton-plugged 250 ml flask containing 25 ml of the following medium: 0.2M Tris buffer (pH 7.6), 100 ml; vitamin-free Casamino acids (Difco), 1.0 g; thiamine, 100 µg; biotin, 100 µg; D-glucose, 2 g; deionized water, 900 ml. Thiamine, biotin and D-glucose were filter-sterilized and added to the autoclaved medium, as in McCarthy and Broda, *J. Gen. Microbiol.*, 1984, 130:2905–2913. The dyes were filter-sterilized and added at 0.005% (w/v) to the autoclaved basal medium. Three replicates of every culture were incubated, and each strain was grown in media supplemented individually with every substrate. Replicate sterile controls also were run in each experiment. Cultures were incubated at 37° C. for 14 days with shaking (200 rpm). Three replicates for each strain growth were incubated in only the basal medium as well.

*P.chrysisporium* was grown in a cotton-plugged 500 ml flask containing 250 ml defined medium (Jeffries, et al., *Appl. Environ. Microbiol.*, 1981, 42:290–296), with the addition of 75 mg adenine (6-aminopurine) and 27 mg L-phenylalanine per liter. This addition accelerated the growth of the fungus without inhibiting ligninase activity. Four substrates were tested: sulfanilic acid, acid yellow 9 and the two synthesized azo dyes; each was separately added at a concentration of about 0.02% (w/v). Cultures were incubated at 37° C. for 7 to 15 days with shaking (250 rpm). Solid agar media were also employed. The medium was 3.0% (w/v) malt extract (Difco Laboratories) agar dispensed in petri plates. The medium also contained 120 mg per liter of specific azo dye.

Protein Determinations

Intracellular protein concentration was used as an index of culture growth. Intracellular protein concentration was determined by boiling harvested culture pellets for 20 minutes in 1M NaOH. Protein concentration was then determined by Sigma colorimetric procedure No. TPRO-562. Extracellular protein was determined using culture filtrates and Bio-Rad colorimteric procedure No. 500-0006.

Spectrophotometric Assay

A one ml sample of actinomycete culture medium was centrifuged and then diluted 2.5-fold with water, or 1.0 ml of fungal supernatant was centrifuged and diluted 5-fold with 10 mM sodium 2,2-dimethylsuccinate buffer (DMS) of pH 4.5. Azo dye substrate present was then measured spectrophotometrically with a Hewlett-Packard 8452 diode array spectrophotometer operated by a PC Vectra computer equipped with HP's MS™-DOS/UV-VIS software. To be certain that changes in substrate spectra were not due to pH variations, the effects of pH on the visible absorption of each compound were also assayed within physiological pH range in the culture media. While the spectra of sulfanilic acid (Max abs at 250 nm), vanillic acid (Max abs at 252 nm and 286 nm) and acid yellow 9 (Max abs at 336 nm) were unaffected by pH over the tested pH range, the spectra of the two novel azo dyes were changed as evidence by shifts of their $Abs_{max}$. Thus, the spectrophotometric assays for these dyes were carried out at their isobestic points. These were, respectively, 450 nm for azo dye 1 and 400 nm for azo dye 2.

High Performance Liquid Chromatography Analysis

Degradation of the dyes and aromatic compounds was confirmed by high performance liquid chromatography. A Hewlett-Packard HP 1090 Liquid Chromatograph equipped with a HP 40 diode array UV-VIS detector and automatic injector was used. The chromatograph was controlled by an HP 9000 series 300 computer which used HP 7995 A ChemStation software. A reverse phase column from Phenomenex (Rancho Palos Verdes Calif., type Spherex 5 C 18 size 250×2.0 mm, serial number PP/6474A) was used. Each 15 minute analysis used a solvent gradient of acetonitrile (solvent A) and 10 mM DMS buffer pH 4.5 (solvent B), with the following conditions: 0 to 5 minutes 100% A; 5 to 12 minutes 25% A 75% B; 12 to 15 minutes 100% B; post time 2 minutes injection volume 10 µl. Absorption was measured at 250, 325, 350, 400 and 450 nm, and spectra were collected automatically by the peak controller.

Preparation of Enzymes and Enzyme Assays

Streptomyces species peroxidases were prepared and assayed using 2,4-dichlorophenol (2,4-DCP) from Sigma Chemical Company as a substrate, as described in Ramachandra, et al., *Appl. Environ. Microbiol.*, 1988, 54:3057–3063. *P.chrysosporium* BKM-F-1767 was grown in a 20-liter carboy containing one liter of nitrogen-limited defined medium (BII-medium), as described by Paszczynski, et al., *Arch Biochem. Biophys.*, 1986, 44:750–765. Preparation and assay of ligninase and manganese peroxidase from these *P.chrysosporium* cultures were carried out as previously reported by Paszczynski, et al., *Methods Enzymol.*, 1988, 161:264–270.

Oxidation of Dyes by Enzyme Preparations

Extracellular enzyme preparations of the Streptomyces species were not observed to produce any detectable decolorization of substrates.

Figure 4A:
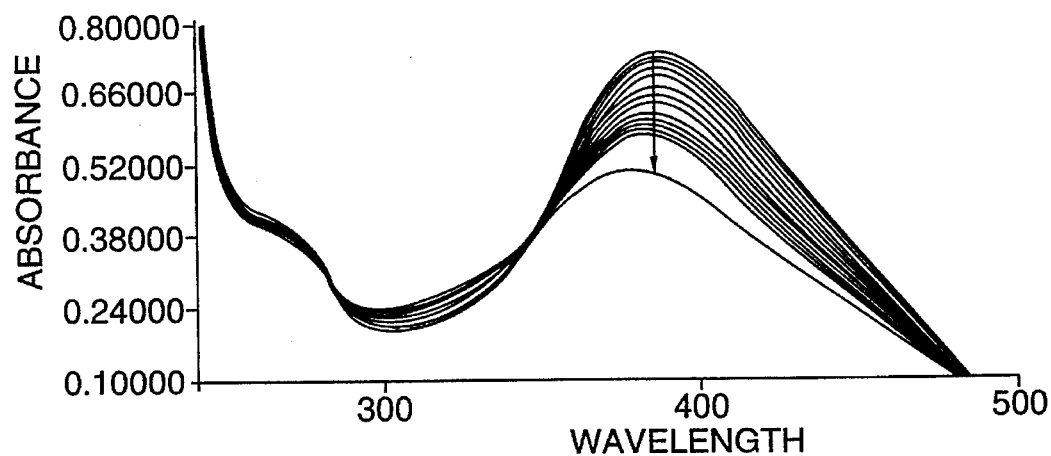
FIG. 4A shows the absorbance spectra over time of acid yellow 9, illustrating its oxidation by *P.chrysosporium* ligninase.
Figure 4B:
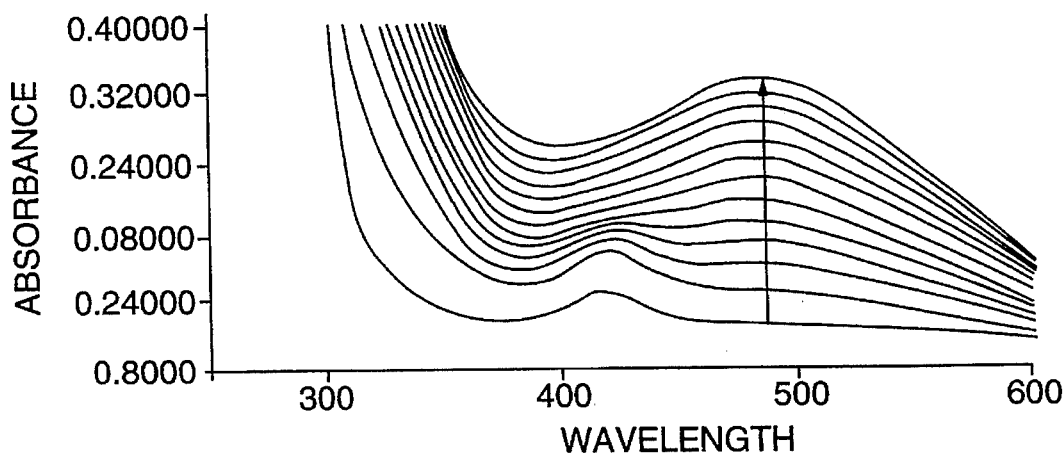
FIG. 4B shows absorbance spectra over time of sulfanilic acid, illustrating its oxidation by *P.chrysoporium* ligninase.

The decolorization of acid yellow 9 azo dye and the oxidation of sulfanilic acid by extracellular preparations of *Phanerochaete chrysosporium* enzymes is shown in FIGS. 4A and 4B, respectively. FIG. 4A shows oxidation of acid yellow 9 by ligninase. The reaction conditions were 0.2 mM hydrogen peroxide, 50 mM sodium tartrate buffer, pH3, 10 µg of dye, and 0.6 units of enzyme (20 µl) in total volume of 1 ml. Cycle time was 30 seconds with the last measure after 15 minutes. During a period of 15 minutes the ligninase exhibited a stable activity which decolorized about 3 micrograms out of 10 micrograms of acid yellow 9 in the reaction mixture.

FIG. 4B shows oxidation of sulfanilic acid which was transformed slowly by ligninase, with an increase in absorbance at about 480 nm. The reaction conditions were the same as for acid yellow 9. No decolorization of the synthesized dyes by ligninase was detected.

Figure 4C:
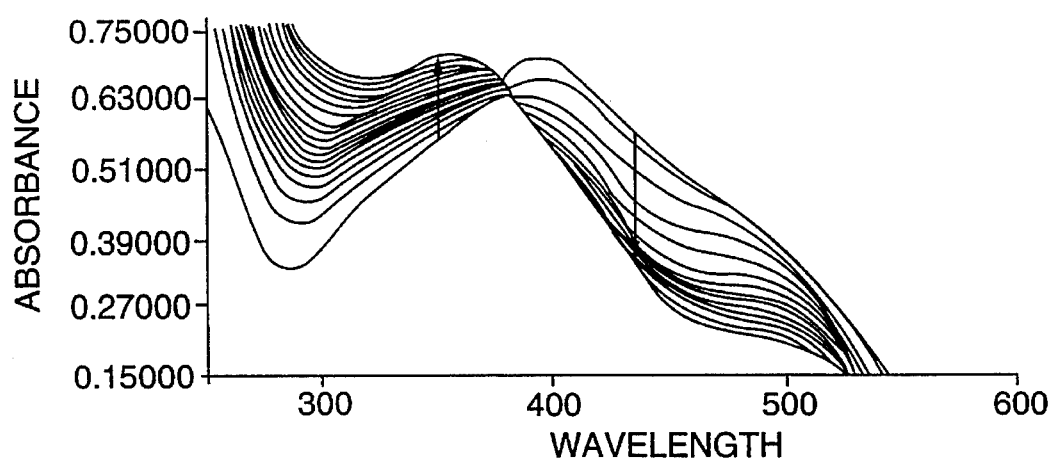
FIG. 4C shows absorbance spectra over time of azo dye 1, illustrating its oxidation by *P.chrysosporium* manganese peroxidase.
Figure 4D:
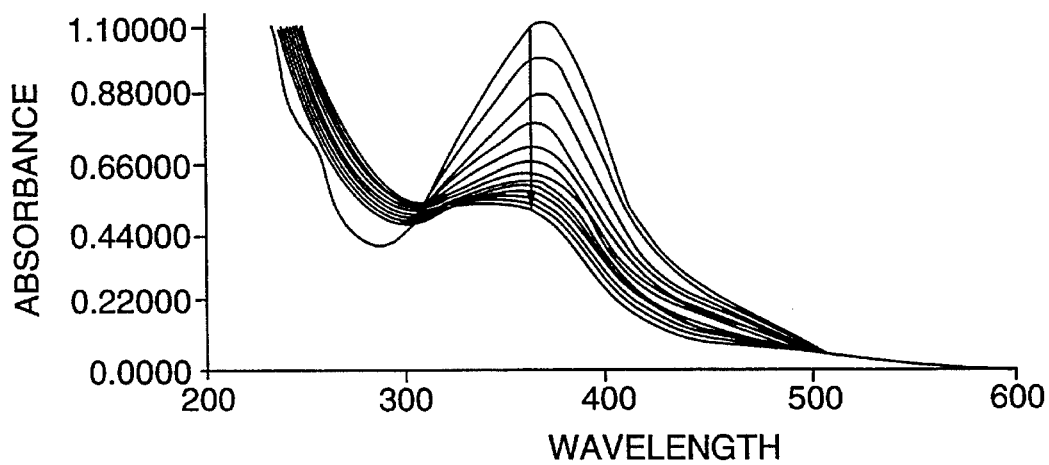
FIG. 4D shows absorbance spectra over time of azo dye 2, illustrating its oxidation by *P.chrysosporium* manganese peroxidase.
Figure 5:
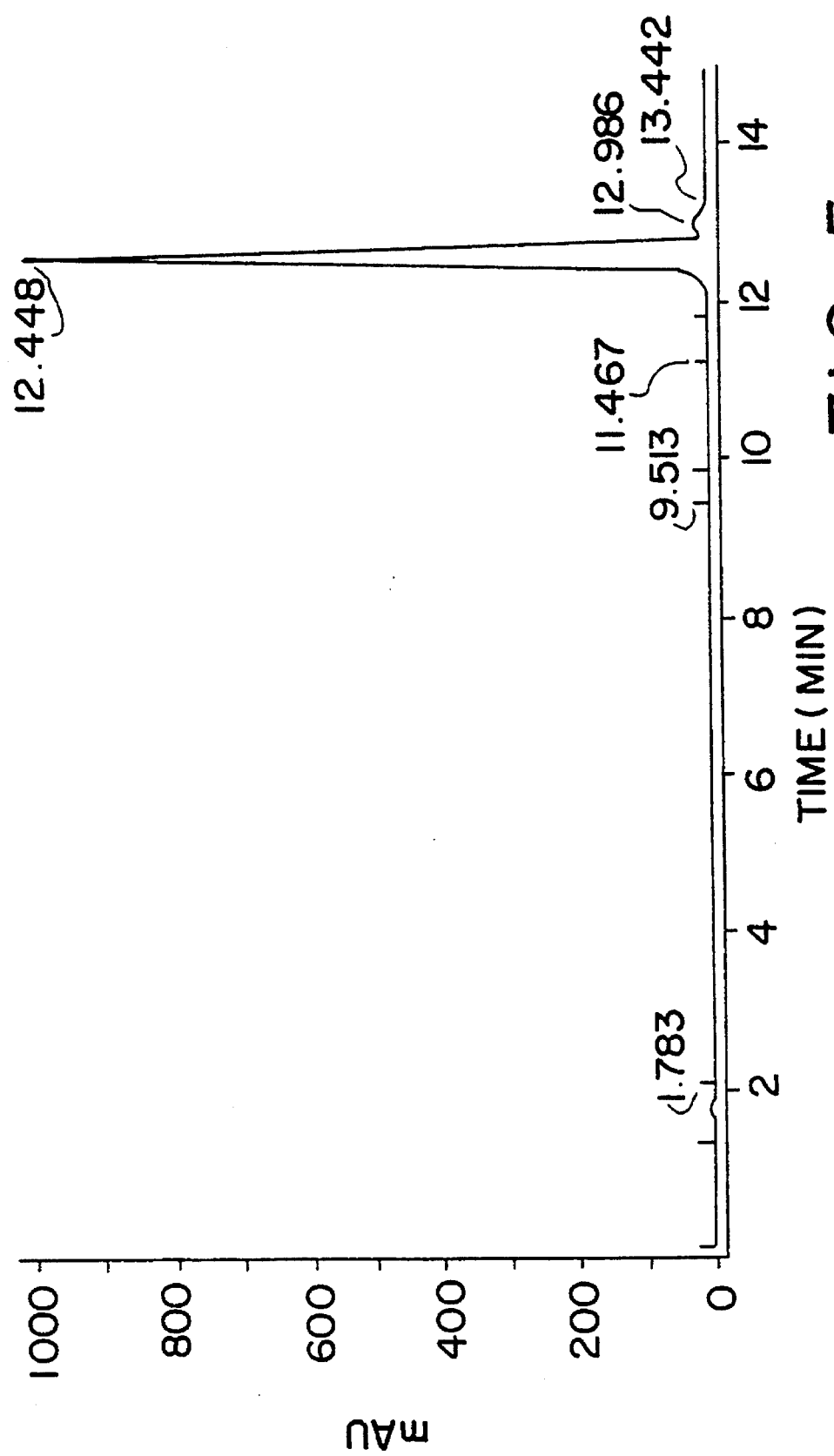
FIG. 5 shows the results of a high performance liquid chromatography (HPLC) of azo dye 1 before (A) and after (B) incubation with *P.Chrysosporium* manganese peroxidase, confirming degradation of the dye and aromatic compounds.

FIGS. 4C and 4D show decolorization of azo dyes 1 and 2 by the manganese peroxidase of *P.chrysosporium* Reaction conditions were 0.2 mM hydrogen peroxide, 50 mM sodium tartrate buffer, pH5, 10 µg dye, 1 unit of enzyme, 1 mM MnSO$_4$ in a total volume of 1 ml. Cycle time was 10 seconds, with the last measure after three minutes of incubation. Oxidation of azo dye 1 by manganese peroxidase resulted in new peak formation at 355 nm. After one hour incubation of azo dye 1 with manganese peroxidase the dye was almost completely degraded comparable to a control chromatogram (FIG. 5). No decolorization of acid yellow 9 or oxidation of sulfanilic acid by manganese peroxidase was detected.

Biotransformation of Microorganisms

Table 1 shows the substrate utilization pattern of the Streptomyces species after a growth period of 14 days. Only six strains (A4, A10, A11, A12, A13, and A14) significantly degraded vanillic acid, while none degraded sulfanilic acid or acid yellow 9 to a detectable extent. Significant degradation was considered degradation greater than about 10%. This result confirms that the compounds characterized by aromatic sulfo group and azo linkages are quite recalcitrant. However, 5 strains (A10, A11, A12, A13, and A14) significantly degraded both the two new azo dyes. Moreover, azo dye 2 was degraded by these strains to a larger extent than azo dye 1.

TABLE 1

Percent substrate removed by cultures of Streptomyces and Phanerochaete during a growth period of 14 and 7 days respectively

| Strain | Sulfanilic acid | Vanillic acid | Yellow #9 | Azo dye #1 | Azo dye #2 |
|---|---|---|---|---|---|
| S. chromofuscus A2 | — | — | — | — | — |
| S. diastaticus A3 | — | — | — | — | — |
| S. rochei A4 | — | 100 | — | — | — |
| S. chromofuscus A6 | — | — | — | — | — |
| S. cyaneus A7 | — | — | — | — | — |
| S. chromfuscus A8 | — | — | — | — | — |
| S. rochei A10 | — | 91 | — | 51 | 74 |
| S. chromofuscus A11 | — | 100 | — | 56 | 89 |
| S. diastaticus A12 | — | 58 | — | 27 | 30 |
| S. diastaticus A13 | — | 34 | — | 15 | 21 |
| S. rochei A14 | — | 72 | — | 43 | 72 |
| S. chromofuscus A20 | — | 5 | — | 1 | 11 |
| S. viridosporus T7A | — | 3 | — | 1 | 9 |
| S. SR-10 | — | — | — | — | — |
| S. badius 252 | — | 7 | — | 9 | 18 |
| P. chrysosporium | 68 | n.d. | 79 | 93 | 94 |

Figure 2:
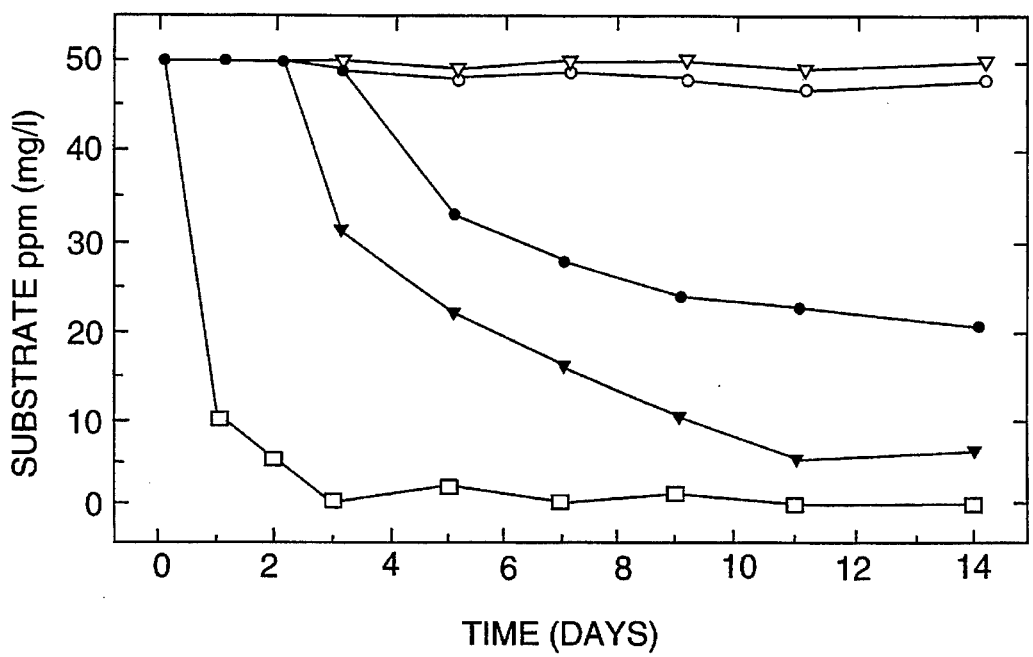
FIG. 2 is a graph showing the degradation by *Streptomyces chromofuscus* A11 of vanillic acid, sulfanilic acid, Acid Yellow 9, and two of the azo dyes synthesized in accordance with the present invention.

FIG. 2 shows the pattern of degradation of each compound by strain *S.chromofuscus* A11 versus time, as a typical example. The graph shows the degradation of vanillic acid (□), sulfanilic acid (∇), acid yellow 9 (○), and azo dyes 1 (●) and 2 (▼). The medium contained 0.2M Tris buffer (pH 7.6), 100 ml; vitamin-free casamino acids, 1.0 g; thiamine, 100 µg; biotin, 100 µg; D-glucose, 2 g; and deionized water, 900 ml. Starting substrate concentrations were 50 ppm.

*S.chrysosporium* degraded sulfanilic acid and acid yellow 9, but only to a limited extent. The vanillic acid, in contrast, was rapidly and thoroughly degraded, as were azo dyes 1 and 2. The ring substitution patterns for vanillic acid, sulfanilic acid and guaiacol are shown below:

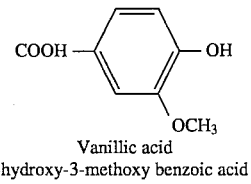
Vanillic acid
4-hydroxy-3-methoxy benzoic acid

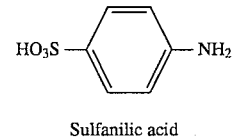
Sulfanilic acid

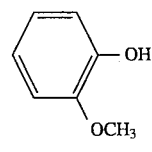
Guaiacol

It appears that the linkage of a guaiacol moiety into azo dye yellow 9 allowed Streptomyces species capable of utilizing vanillic acid to decolorize an azo dye that the Streptomyces could not otherwise transform. The only vanillic acid degrader that could not attack either azo dyes 1 or 2 was *S.rochei* A4, possibly because this strain catabolizes vanillic acid by attacking its carboxylic acid group, a substituent absent in the guaiacol moiety. Hence, utilization of the two dyes appears to start at the guaiacol substituent, but the pathway used by these Streptomyces remains to be elucidated.

Figure 3:
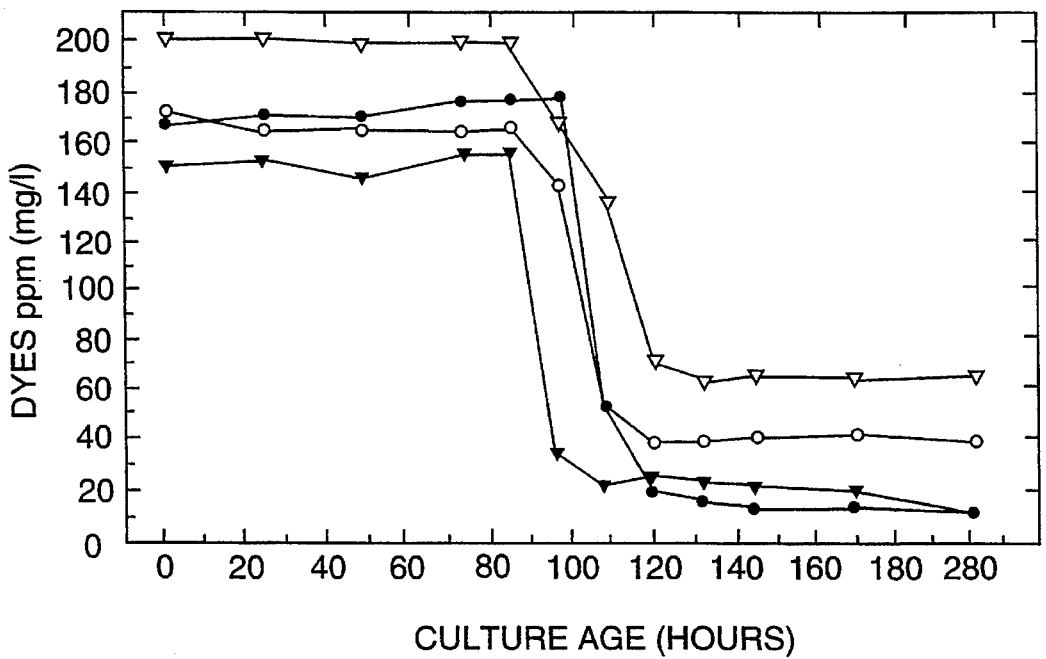
FIG. 3 is a graph showing the rate of degradation by *Phanerochaete chrysosporium* of three azo dyes and sulfanilic acid.

The Phanerochaete fungus almost completely (90%) degraded azo dyes 1 and 2 after a growth period of seven days as shown in FIG. 3. The graph shows decolorization or removal by *P.chrysosporium* of sulfanilic acid (∇), acid yellow 9 (○), azo dye 1 (●), and azo dye 2 (▼). Agitated cultures were grown at 37° C. in a mineral medium supplemented with phenylalanine, and starting dye concentrations were 150–200 ppm. There was a characteristic lag of 80–90 hours prior to degradation of any of the compounds by the fungus due to slower growth compared to the Streptomyces. On the solid medium, *P.chrysosporium* behaved similarly leaving some undegraded color after two weeks of growth. *P.chrysosporium* apparently degrades using its ligninolytic enzymes.

In this work several times higher concentrations of azo dyes were used than reported earlier by Cripps. The ability of this organism to oxidize sulfonated azo aromatic compounds was also tested, shown in FIG. 3 and Table 1. The maximum rate of decolorization occurred on the fourth day of growth in the BII medium for all of the compounds. However, in the cultures with yellow 9 or sulfanilic acid, as assayed by spectrophotometric and HPLC analysis, some undegraded dye remained in the medium after decolorization ended. Yet using HPLC, the inventors were not able to detect any residual substrate in the culture broth after 1 week of growth, even though color was still present in the culture filtrates. One explanation is the finding of Kulla, et al., supra, who found that in cultures of Pseudomonas which were actively degrading azo dyes, secondary oxidative coupling occurred between sulfonated and nonsulfonated phenols, giving dead-end polymers resistant to further degradation.

In testing which, if either, of the ligninolytic peroxidases of *P.chrysosporium* was involved in the degradation of these azo compounds, it was found that ligninase oxidized yellow 9 and sulfanilic acid (FIG. 4A and B), while manganese peroxidase oxidized azo dyes 1 and 2 (FIG. 4C and D). The HPLC analysis of the reaction mixture after incubation of azo dye 1 with manganese peroxidase revealed polymorphic reaction products (FIG. 5B). Oxidation of sulfanilic acid by ligninase produced a purple unstable product, which upon exposure to air precipitated. During a 15-minute incubation period, oxidation of yellow 9 or sulfanilic acid by manganese peroxidase was not detected, nor the oxidation of azo dye 1 or 2 by ligninase. Thus, it is possible that ligninases may cooperate in the degradation of azo dyes 1 and 2.

Azo dyes 1 and 2 were decolorized to a greater extent by *P.chrysosporium* than was acid yellow 9 (Table 1). Even greater decolorization was noted during the growth of *S.chromofuscus* A11 (FIG. 2). These results show that linkage of a guaiacol molecule into the dye structure increased its susceptibility to degradation. Azo dye structures are typically conjugated multi-unsaturated systems. This makes it possible to change only one fragment of the molecule and yet have the entire conjugated system become accessible to enzymatic attack, particularly with microorganisms like white-rot fungi that use oxidative enzymes that generate cation radicals. This finding has general application for synthesizing more easily biodegradable azo dyes and other recalcitrant compounds in accordance with the present invention.

Biotransformation of Azo Dyes 3–19

Table 2 shows the concentrations of azo dyes 2–19 after cultivation with *P.chrysosporium* for ten days on mineral medium.

TABLE 2

Concentration of Substrates After Ten Days Cultivation with *P. chrysosporium*

| Azo-comp number | Beginning Concentrations | | | |
|---|---|---|---|---|
| | 100 ppm | 150 ppm | 200 ppm | 300 ppm |
| 2 | 2.493 | 6.350 | 10.068 | 7.318 |
| 3 | 0.358 | 1.223 | 1.894 | 114.772 |
| 4 | 1.637 | 3.763 | 4.218 | 16.323 |
| 5 | 6.084 | 9.870 | 14.500 | 22.680 |
| 6 | 12.909 | 14.003 | 33.309 | 39.326 |
| 7 | 62.893 | 41.044 | 10.200 | 246.044 |
| 8 | 16.079 | 28.401 | 29.704 | 135.680 |
| 9 | 81.911 | 109.822 | 32.044 | 153.733 |
| 10 | 8.135 | 15.279 | 46.588 | 42.897 |
| 11 | 6.795 | 14.416 | 30.075 | 21.765 |
| 12 | 2.368 | 44.227 | 6.160 | 198.240 |
| 13 | 7.734 | 20.776 | 28.216 | 20.096 |
| 14 | 4.411 | 11.843 | 15.529 | 36.800 |
| 15 | 1.901 | 10.589 | 17.931 | 17.791 |
| 16 | 67.801 | 92.683 | 179.300 | 219.079 |
| 17 | 29.803 | 58.942 | 93.250 | 136.057 |
| 18 | 8.387 | 20.342 | 40.875 | 77.099 |
| 19 | | 2.938 | | 252.592 |

Table 3 shows the concentration of azo dye substrates after cultivation with Streptomyces strains A10, A11, A12, and A13.

TABLE 3

Percent Degradation of Substrates After Streptomyces Cultivation

| Substrates | Wavelengths | Degradation (%) Strains | | | |
|---|---|---|---|---|---|
| | | A10 | A11 | A12 | A13 |
| 2 | 396 | 77 | 73 | 43 | 18 |
| 3 | 396 | 68 | 73 | 39 | 10 |
| 4 | 416 | 79 | 83 | 39 | 8 |
| 5 | 386 | 9 | 20 | 3 | 8 |
| 6 | 376 | — | — | — | — |
| 7 | 430 | — | — | — | — |
| 8 | 422 | — | — | — | — |
| 9 | 420 | — | — | — | — |
| 10 | 394 | 11 | 16 | 7 | 6 |
| 11 | 420 | 4 | 9 | — | — |
| 12 | 376 | — | — | — | — |
| 13 | 376 | 2 | 5 | 1 | 1 |
| 14 | 466 | — | — | — | — |
| 15 | 474 | 2 | 3 | 1 | 1 |
| 16 | 350 | — | — | — | — |
| 17 | 408 | — | — | — | — |
| 18 | 386 | — | — | — | — |

—=no degradation

The Streptomyces were grown on the same media and under the same conditions as previously described. Spectroscopic analysis of substrates 14, 15, 16, 18 was unaffected by pH over the tested pH range. However, the $Abs_{max}$ of the substrates 1 to 12 shifts with pH changes. Thus the spectrophotometric assays for substrates 1 to 12 were carried out at their specific isosbastic points.

Degradation was calculated as percent of substrates removed from culture broth, considering the evaporation factor (around 10%). The substrates' concentrations have been calculated versus standard curves prepared for each dye (0–50 μg) at the chosen wavelength; standard curves over the tested concentrations were linears.

VERATRYL ALCOHOL ADDITION

*Phanerochaete chrysosporium* decolorized several polyaromatic azo dyes in ligninolytic culture. The oxidation rates of individual dyes depended on their structures. Veratryl alcohol (VA) stimulated azo dye oxidation by pure lignin peroxidase (ligninase, LiP) in vitro. Accumulation of compound II of lignin peroxidase, an oxidized form of the enzyme, was observed after short incubations with these azo substrates. When veratryl alcohol was also present, only the native form of lignin peroxidase was observed. Azo dyes acted as inhibitors of veratryl alcohol oxidation. After an azo dye had been degraded, the oxidation rates of veratryl alcohol recovered, confirming that these two compounds competed for ligninase during the catalytic cycle. Veratryl alcohol acts as a third substrate (with $H_2O_2$ and the azo dye) in the lignin peroxidase cycle during oxidations of azo dyes.

Veratryl alcohol (3,4-dimethoxybenzyl alcohol) is a secondary metabolite found in ligninolytic cultures of *Phanerochaete chrysosporium*. Veratryl alcohol is synthesized de novo by way of phenylalanine, 3,4-dimethoxycinnamyl alcohol, and veratryl glycerol. The onset of ligninolytic activity and glucose oxidation leading to hydrogen peroxide production by *P. chrysosporium* appears simultaneously with the accumulation of VA in cultures.

The onset of ligninolytic activity in *Phanerochaete chrysosporium* requires VA, but the relationship between the concentration of VA produced by various strains of *P.chry-* sosporium and their mineralization of lignin is not clear. Studies with whole cultures of *P. chrysosporium* indicate function for VA might be to protect ligninase against inactivation by hydrogen peroxide. This has been confirmed by experiments where high concentrations of hydrogen peroxide were added to non-protein-synthesizing cultures. The concentration of VA necessary for protection of ligninase activity was in direct proportion to the rate of hydrogen peroxide synthesis by the cultures.

Using pure ligninase preparations, we investigated the degradation of several complex azo dyes by *P. chrysosporium*. Oxidations of VA and azo compounds could be monitored simultaneously since they have considerably different absorption maxima. Our results suggested that LiPI (lignin peroxidase compound one), formed during oxidation of $H_2O_2$ by LiP, oxidized polyaromatic azo dyes, forming LiPII. LiPII was then reduced back to the native enzyme by oxidation of VA.

Decolorization of some azo dyes by LiP was almost totally dependent on the presence of VA. VA significantly increased the oxidation rates of these azo dyes. A simultaneous inhibition of LiP-catalyzed VA oxidation by azo compounds was observed. When azo dye oxidations were terminated, the rates of VA oxidation recovered. These observations suggest that LiPI is able to oxidize these dyes, but the LiPII formed requires VA to recycle to the native state. Similar enzymatic oxidation interactions could be involved during degradation of lignin and other recalcitrant compounds.

Materials and Methods

Dyes. Azo dye No. 20 Congo Red (Direct Red No. 28) [international no. 573-58-01], No. 21 Acid Red 114 [6459-94-5], No. 22 Direct blue 51, and Biebrich Scarlet [4196-99-0], No. 25 Direct Blue 71 [4399-55-7], No. 26 Direct Red 75 [2828-43-8], No. 27 Chrysophenine [2870-32-8], No. 28 Tetrazine [1934-21-0], No. 29 Direct Yellow 27, and veratryl alcohol were purchased from the Aldrich Chemical Co. All other chemicals were reagent or HPLC grade, and were used as purchased.

Organism and culture conditions. *P. chrysosporium* Burds BKM-F-1767 (ATCC 24725) was obtained from the USDA Forest Products Laboratory, Madison, Wis. The fungus was maintained and spore inocula were prepared as previously described (Huynh and Crawford, FEMS Microbiol. Lett. 28:119–123 (1985)). For production of LiP, 1-liter cultures were grown under nitrogen limitation and 100% oxygen in the medium described by Bonnarme and Jeffries, Appl. Environ. Microbiol. 56:210–217 (1990) in a 10-liter rotated carboy as described previously (Paszczynski et al., Arch. Biochem. Biophys 244:750–765 (1986)). Culture conditions for degradation of azo dyes were described earlier (Paszczynski et al., Enzyme Microb. Technol. 13:378–384 (1991)).

Degradation of azo dyes. Decolorizations of dyes in cultures were monitored at their absorption maxima at pH 4.5, or using HPLC. For HPLC we used a Spherisorb ODS2 C18 column with a sequence of DMS buffer at pH 4.5 and acetonitrile as solvents (5 min 100% DMS, 15 min 100% acetonitrile, 18 min 100% acetonitrile, 19 min 100% DMS, 20 min 100% DMS, 5 min postran 100% DMS). Peaks were monitored at 260 and 450 nm. Results from spectrophotometric and HPLC methods were compared.

Enzyme assays. Lignin peroxidase activity was determined spectrophotometrically at room temperature with VA as substrate. One U of enzyme activity was defined as 1 μmole of veratryl aldehyde formed per min at pH 3. Simultaneous oxidations of azo dyes and veratryl alcohol were measured using a Hewlett-Packard 8452 diode array spectrophotometer operated in the kinetic mode by a Vectra PC equipped with MS™-DO/UV-VIS software. Azo dye concentrations were determined by measuring absorbances at appropriate maxima Dye 24 shows $E_{(506)}=5.07\times10^4$ $M^{-1}$ $cm^{-1}$, and dye 28 shows $E_{(430)}=4.12\times10^4$ $M^{-1}$ $cm^{-1}$.

Table IV shows the decolorization of individual azo dyes by a ligninolytic culture of *P.chrysosporium* after ten days of growth. The initial concentration of dye was 200 mg per liter. Numbers represent mg per liter of dye remaining in the cultures.

TABLE IV

| | Analytic Methods | | |
|---|---|---|---|
| Azo Dye | HPLC | Spectrophotometry | Amount Degraded (av. %) |
| 20 | 62.20 | 52.01 | 71.45 |
| 21 | 103.62 | 102.38 | 48.50 |
| 22 | 12.28 | 7.64 | 95.02 |
| 23 | 72.43 | 89.27 | 59.57 |
| 24 | 4.43 | 1.11 | 98.61 |
| 25 | 14.86 | 9.66 | 93.87 |
| 26 | 6.98 | 4.33 | 97.17 |
| 27 | 29.42 | 28.33 | 85.56 |
| 28 | 3.00 | 2.42 | 98.64 |
| 29 | 109.39 | 108.92 | 45.42 |

Dyes 20 to 26 contain naphthalene.
Cultures with dyes 24 and 28 were complete bleached.

Enzyme purification. After six days of growth, when the specific activity of ligninase reached about 250 U per liter, culture filtrates were separated from mycelial debris by filtration. One liter of culture filtrate was concentrated to about 10 ml using an Amicon PM-10 membrane and desalted in 10 mM sodium acetate buffer (pH 6) using a Sephadex G25 NAP10 column. Ligninase isoenzyme was separated from Mn-dependent peroxidases using a Pharmacia fast protein liquid chromatography system equipped with a Mono Q HR 5/5 column following methods described elsewhere (25). In this study isoforms H2 and H8 were used. The purified proteins were electrophoretically homogenous and showed $A_{408}/A_{280}$ of about 4.5.

Figure 7A:
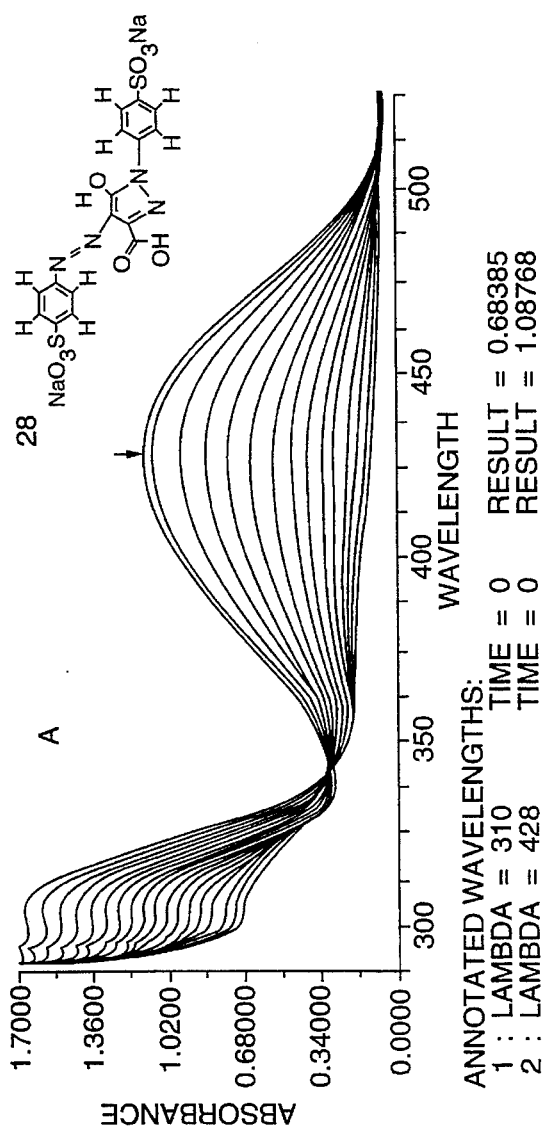
FIG. 7A shows the oxidation of veratryl alcohol and azo dye 28 by lignin peroxidase.
Figure 7B:
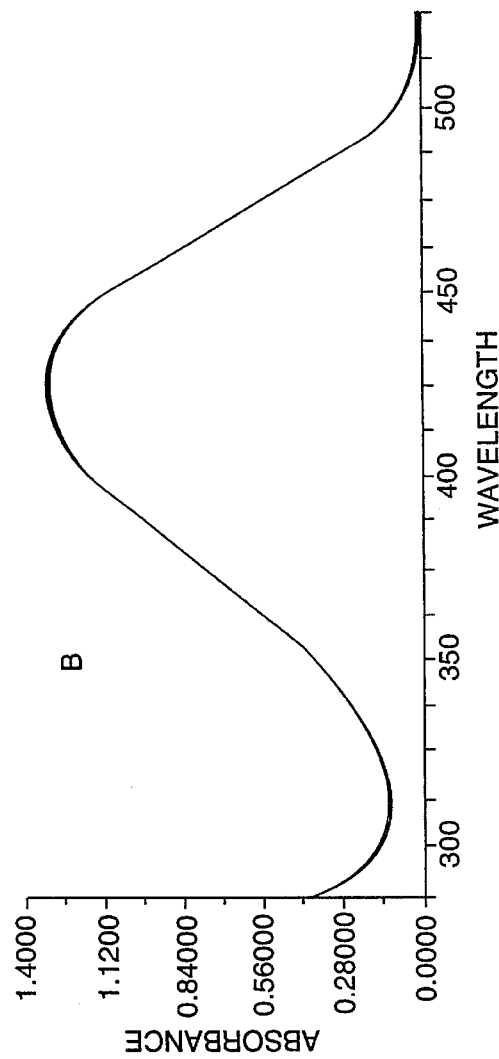
FIG. 7B shows the oxidation of azo dye 28 in the absence of veratryl alcohol.

Oxidation Of azo dyes. In vitro studies were limited to dyes 24 and 28. Ligninase without VA oxidized azo dyes 24 and 28, but only to a very limited extent. After VA was added to the reaction mixtures, oxidation of both substrates began, leading to total decolorization of the dyes. FIGS. 1A and 2A show the simultaneous oxidation of azo dyes and VA by ligninase. Without VA, azo dye oxidation was very limited and terminated rapidly (FIGS. 6B and 7B). When a dye was present in a reaction mixture, the rate of VA oxidation decreased due to an apparent competition for LiPI between these two compounds. The oxidation rate of VA recovered when the azo dye oxidation was completed (FIG. 8). Under our conditions the maximal rate of VA oxidation was about 159 AU (absorption change per min per ml of ligninase solution). Wavelengths of 310 nm for VA, 506 nm for dye 24, and 430 nm for dye 28 oxidations were used in monitoring substrate removal. We observed that the oxidation of azo dyes is stimulated by VA in high (200 μM) and low (20 μM) $H_2O_2$ concentrations. These results establish that ligninase is capable of oxidizing recalcitrant azo dyes effectively only when VA is present.

Form of Liginase in Reaction Mixtures With and Without VA

Figure 9:
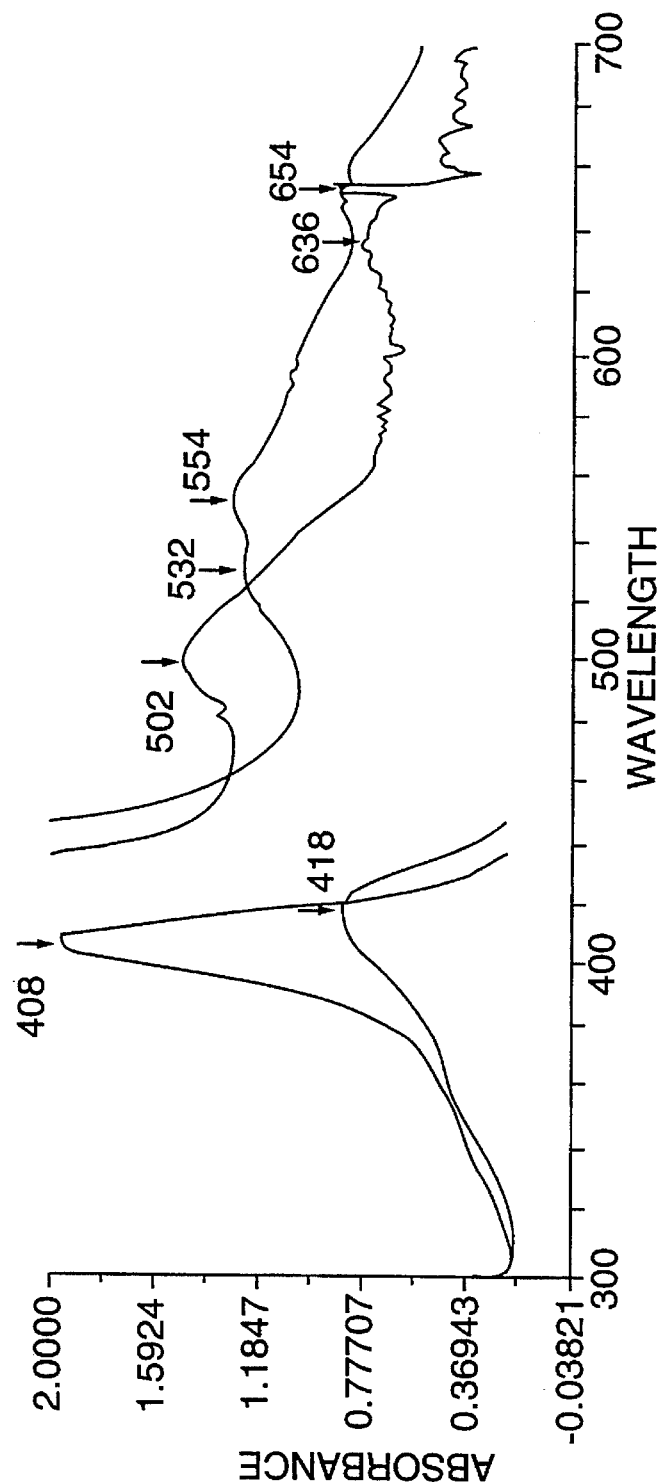
FIG. 9 shows the absorption rate of ligninase in the reaction mixture with veratryl alcohol.

Ligninases from two parallel reaction mixtures were recovered by Sephadex G25 gel filtration, and spectra were recorded (FIG. 9). The first reaction mixture contained 50 mM sodium tartrate at pH 3, 18 µM enzyme, 0.2 mM $H_2O_2$, 15 µg of dye 28, and 1 mM VA. In the second reaction mixture, VA was excluded. We observed the spectrum of the native enzyme in the reaction mixture that had contained VA, and the spectrum of LiPII in the reaction mixture that had not contained VA, in which only the azo dye was available as a reductant. Dye 24 and 28 gave similar results. In conclusion, the results presented suggest that only the highest oxidation stage of ligninase (LiPI) is able to attack azo dyes, and that the presence of VA helps to complete the catalytic cycle of the enzyme.

The present invention provides a biodegradable dye compound comprising an azo group having first and second nitrogen atoms linked to first and second aromatic rings, wherein the first aromatic ring has a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$.

The present invention also provides a biodegradable composition comprising (1) an azo dye having first and second nitrogen atoms linked to first and second aromatic rings, the first ring having a lignin-like substitution pattern, (2) an amount of lignin peroxidase effective to degrade said dye, wherein lignin peroxidase is converted to lignin peroxidase II as the dye is degraded, and (3) an amount of veratryl alcohol effective to recycle lignin peroxidase II to lignin peroxidase. An effective amount of lignin peroxidase is defined to mean an amount sufficient to oxidize the azo dye to an oxidized state. An amount of veratryl alcohol effective to recycle ligninperoxidase to ligninperoxidase II is suitably, for example, at least 20 micromoles, and can be 200 micromoles or greater. The lignin peroxidase may be provided by a microbe.

The first ring may have a first substituent $R_1$ selected from the group consisting of hydroxy, alkoxy and amino, and a second substituent $R_2$ selected from the group consisting of hydrogen, lower alkoxy, lower alkyl and halogen. The first aromatic ring may also have a first substituent $R_1$ selected from the group consisting of hydroxy, lower alkoxy, or amino, and a second substituent $R_2$ selected from the group consisting of lower alkyl, lower alkoxy and halogen. The first aropmatic ring may have a third ring substituent $R_3$ selected from the group consisting of lower alkyl, lower alkoxy, and halogen. The azo dye may further comprise a plurality of azo groups having nitrogen atoms linked to aromatic rings such that the compound is a fully conjugated system. Finally, the first aromatic ring may have a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$.

The present invention also provides a method for degrading xenobiotic azo dyes having first and second nitrogen atoms linked to first and second aromatic rings, the method comprising the steps of (1) providing a lignin-like substitution pattern on the first aromatic ring, and (2) exposing the mixture to an amount of lignin peroxidase effective to degrade the azo dye, wherein lignin peroxidase is converted to lignin peroxidase II as the dye is degraded. The ligninperoxidase may be provided by a microbe, such as *P.chrysosporium*. The method may also include the step of combining veratryl alcohol with the azo dye to form a mixture and exposing the mixture to lignin peroxidase, wherein the veratryl alcohol is added in an amount sufficient to convert lignin peroxidase II to lignin peroxidase.

Lignin-Like Structures

As the data in Tables 1–3 demonstrate, the biodegradability of xenobiotics, such as azo dyes, can be enhanced by attaching lignin-like structures to them. Lignin-like structures are those that are contained in lignin and which enhance biodegradability of xenobiotic azo dyes when they are attached to them. Lignin-like structures also include analogous chemical structures which are not known to be in lignin, yet sufficiently resemble lignin structures to provide enhanced biodegradability.

Chemical and spectrometric studies of softwood lignin indicate that lignin is an aromatic polymer in which the monomeric guaiacylpropane units are connected by both ether and carbon-carbon linkages. Several substructures in lignin macro-molecules include guaiacylglycerol-β-aryl ether (β-O-4' substructure 1) which is the most abundant interphenylpropane linkage (40–60%) in lignin, followed by phenylcoumaran (β-5' substructure 2; 10%), diarylpropane (β-1' substructure 3; 5–10%), pinoresinol (β-β' substructure 4; 5%), biphenyl (5-5' substructure 5; 10%), diphenyl ether (4-O-5' substructure 6; 5%), and others.

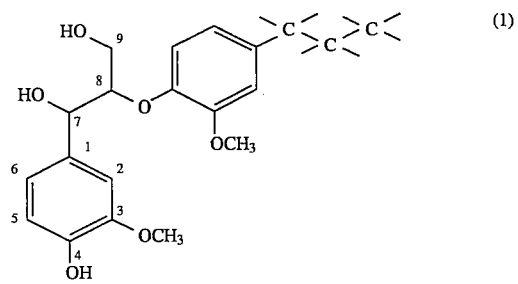

(1)

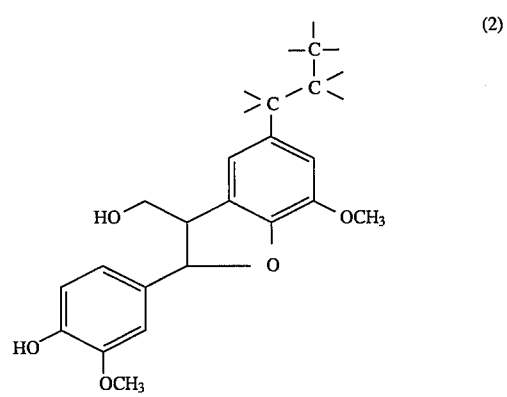

(2)

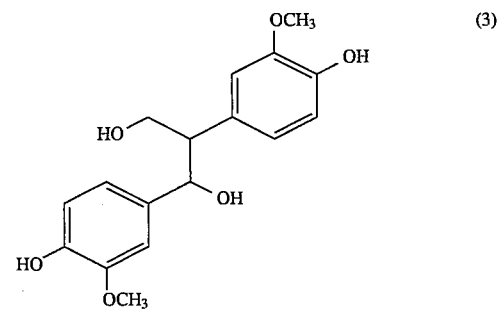

(3)

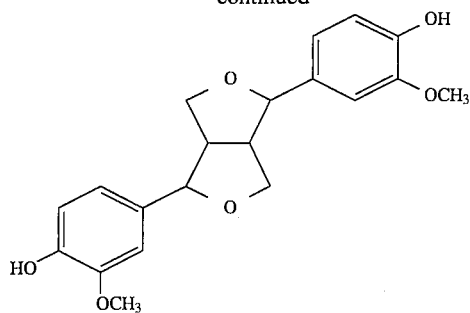
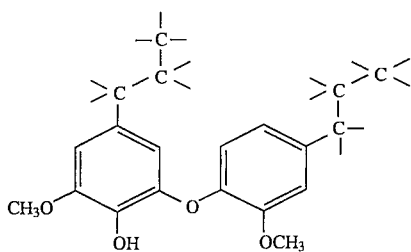
(5)
(6)
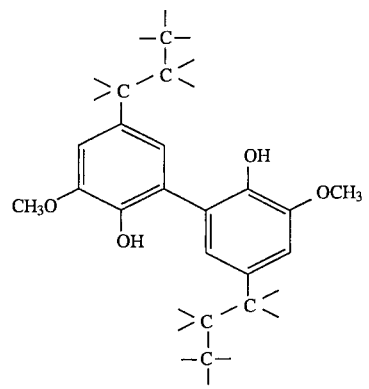
A structure model of softwood lignin is described in Higuchi, *Biosynthesis and Biodegradation of Wood Components*, Wood Research Institute, Kyoto, Japan, 1985, page 143, and set forth below to show the variety of ring substitutions present in lignin.

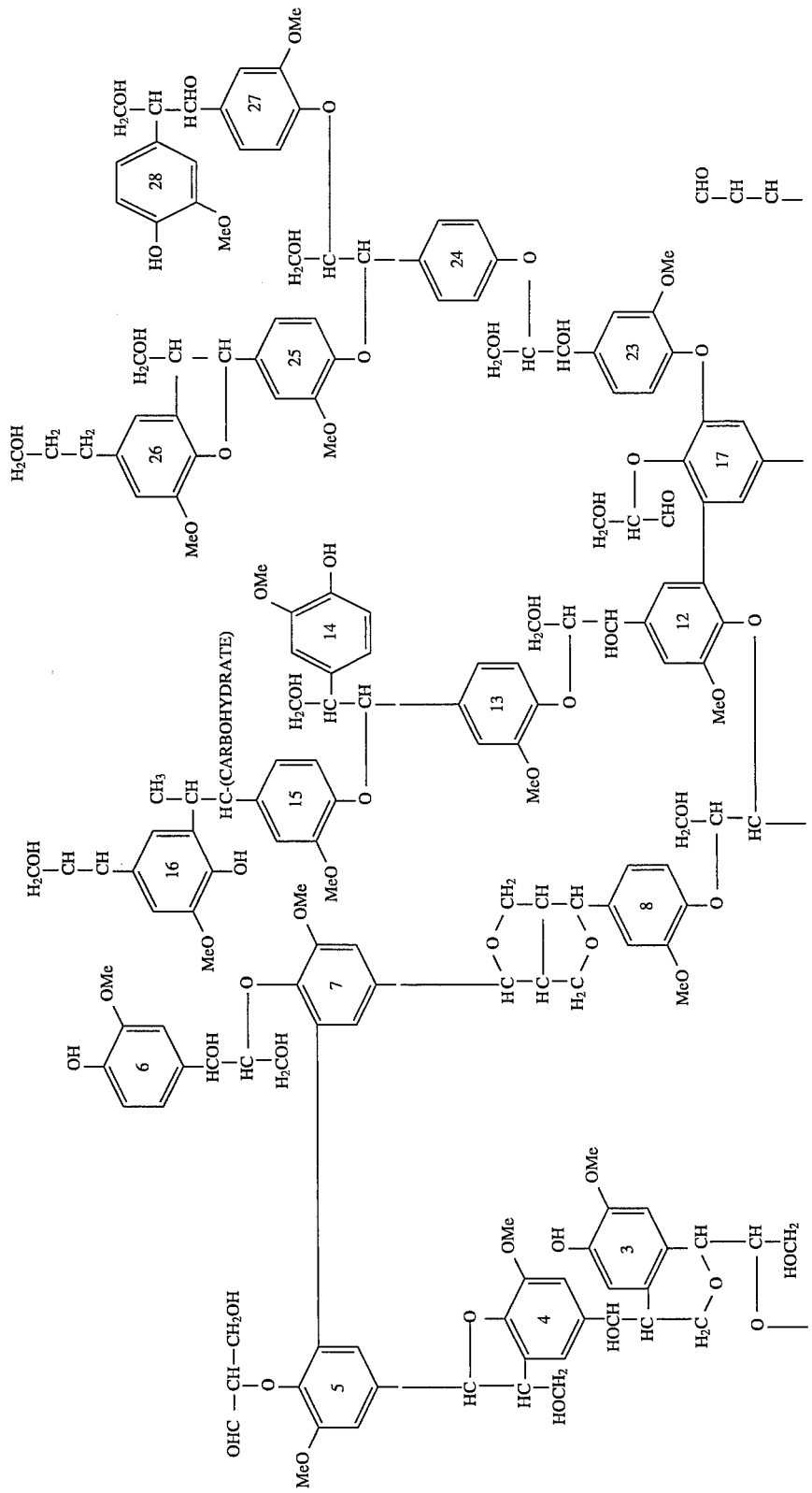

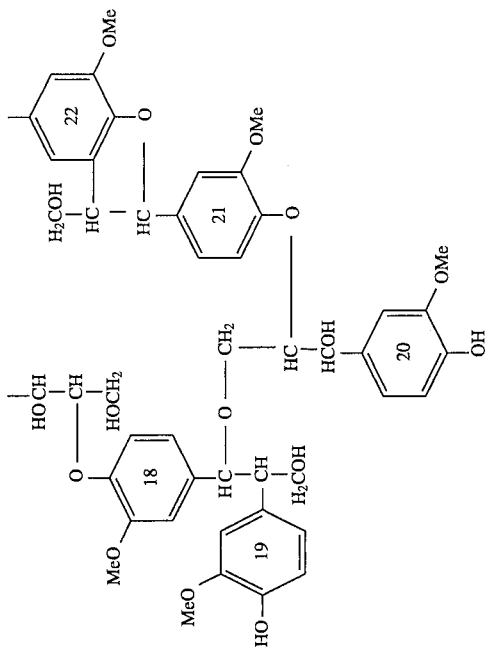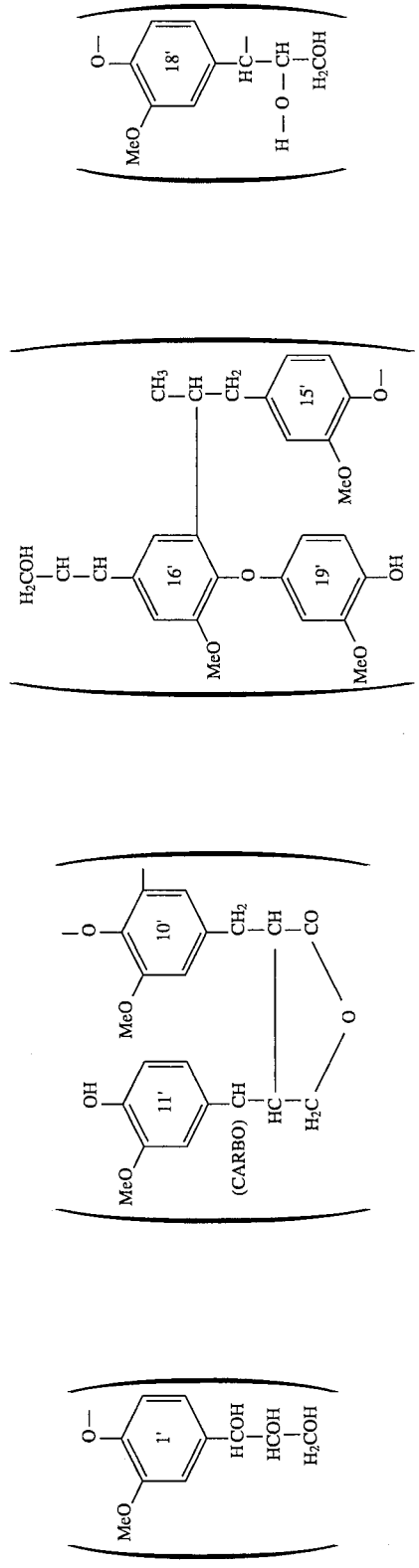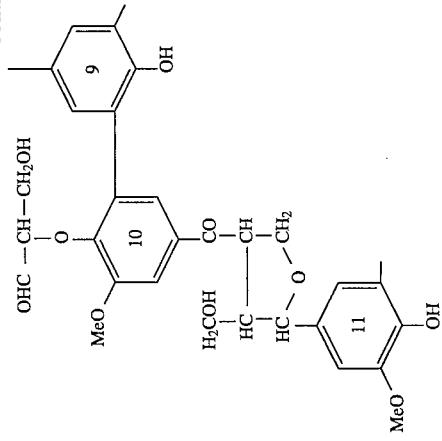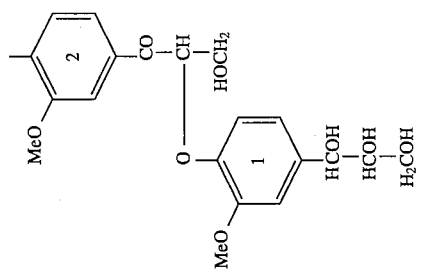

The composition of lignin varies for different kinds of lignins. The lignin of hardwoods such as beech, for example, is composed of approximately equal amounts of guaiacyl- and syringylpropane units connected by linkages similar to those found in spruce lignin. Grass lignin, such as bamboo lignin, is considered to be composed of guaiacyl-, syringyl-, and p-hydroxyphenyl.

The biodegradable azo dyes of the present invention include an azo group having a nitrogen atom linked to an aromatic ring, in which the ring has a lignin-like substitution pattern. As used herein, the term "lignin-like substitution pattern" refers to a ring having substituents which provide a lignin-like structure. In its simplest embodiments, the lignin-like substitution pattern provides guaiacyl or syringyl units connected by a nitrogen linkage to the remainder of the azo dye. The present inventors have found that biodegradability is especially enhanced by providing a lignin-like aromatic ring in which a first ring substituent $R_1$ is selected from the group consisting of hydroxy, lower alkoxy or amino, and a second substituent $R_2$ is selected from the group consisting of lower alkyl, lower alkoxy and halogen. In especially preferred embodiments, a third ring substituent $R_3$ is selected from the group consisting of lower alkyl, lower alkoxy and halogen.

It is preferred, although not necessary, that the azo dye be a fully conjugated system. In particular embodiments, the dye includes a plurality of azo groups having nitrogen atoms linked to aromatic rings such that the compound is a fully conjugated system. Diazo or triazo compounds, for example, would provide such a fully conjugated system. Such fully conjugated systems are both brighter and more susceptible to degradation. However, some less than fully conjugated dyes (such as C.I. direct red 75; C.I direct orange; C.I. direct red 250; and C.I. direct yellow 27) may also be modified by adding lignin-like moieties to make them more biodegradable. Modification of a portion of the dye molecule will at least make that part of the molecule more degradable, and may as a result make the entire molecule more degradable.

The aromatic ring having the lignin-like substitution pattern can be benzyl, naphthyl or other aromatic structures. A naphthyl ring is shown in azo dye 19. The dye may preferably include a sulfonic acid group to increase solubility of the dye. The sulfonic acid group may be present on either the lignin-like ring (as in dyes 18 or 19) or elsewhere in the molecule.

In particular embodiments, R2 is ortho to R1. In other embodiments, R1 is hydroxy while R2 is a lower alkoxy, such as methoxy, or a lower alkyl group such as methyl or ethyl. In preferred embodiments wherein R1 is hydroxy, R2 may preferably be halogen, such as fluorine or chlorine.

The azo dyes of the present invention preferably include at least one sulfonic acid group, on either the lignin-like ring or somewhere else in the molecule, to increase the solubility of the azo compound. This solubility is important to some dye applications.

In those embodiments in which R2 is ortho to R1, R2 may preferably be lower alkyl, lower alkoxy or halogen.

Several embodiments of the invention have been found to be particularly suitable for significant degradation by Phanerochaete. These embodiments include the following azo dyes: 4-dimethylamino-azobenzene-4' -sulfonic acid, 4-diethylamino-azobenzene-4'-sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene- 4'-sulfonic acid, 3-sec-butyl-4-hydroxy-azobenzene- 4'-sulfonic acid, 2-hydroxy-5-methyl-azobenzene- 4'-sulfonic acid, 2-hydroxy-5-ethyl-azobenzene4'-sulfonic acid, 3,5-dimethyl-4-hydroxy-azobenzene-4' -sulfonic acid, 3,5-dimethoxy-4-hydroxy-azobenzene-4' -sulfonic acid, 3,5-difluoro-4-hydroxy-azobenzene-4,sulfonic acid, 2-hydroxy-4,5-dimethyl-azobenzene-4' -sulfonic acid, 2-hydroxy-3-methoxy-5-methyl-azobenzene-4' -sulfonic acid.

Specific Embodiments

In a particular embodiment, the biodegradable dye compound comprises an azo group having first and second nitrogen atoms linked to first and second aromatic rings wherein the first aromatic ring has a first substituent $R_1$ selected from the group consisting of hydroxy and lower alkoxy, a second substituent $R_2$ selected from the group consisting of lower alkyl and lower alkoxy, and a third substituent $R_3$ selected from the group consisting of lower alkoxy and halogen.

In other embodiments, $R_3$ is halogen or may be selected from the group consisting of fluorine and chlorine.

In other embodiments, the azo dye further includes at least one sulfonic acid group.

In yet other embodiments $R_3$ is halogen.

In yet other embodiments, $R_1$ is hydroxy and $R_2$ and $R_3$ are both ortho to $R_1$; or $R_1$ is hydroxy and $R_2$ and $R_3$ are methoxy; or $R_1$ is hydroxy and $R_2$ is methyl and $R_3$ is methoxy.

In yet other embodiments $R_3$ is lower alkyl or lower alkoxy.

In still other embodiments, the biodegradable azo dye is selected from the group consisting of 3,5-dimethyl-4-hydroxy-azobenzene-4'-sulfonic acid; 3,5-dimethoxy-4 -hydroxy-azobenzene-4'-sulfonic acid; 3,5-difluoro-4 -hydroxy-azobenzene-4'-sulfonic acid; 2-hydroxy-4,5 -dimethyl-azobenzene-4'-sulfonic acid; and 2-hydroxy-3 -methoxy-5-methyl-azobenzene-4'-sulfonic acid.

In yet other embodiments the biodegradable azo dye compound is selected from the group consisting of 3,5 -dimethyl-4-hydroxy-azobenzene-4'-sulfonic acid, 3,5 -dimethoxy-4-hydroxy-azobenzene-4'-sulfonic acid, and 2 -hydroxy-3-methoxy-5-methyl-azobenzene-4'-sulfonic acid.

In other embodiments, the dye compound comprises an azo group having first and second nitrogen atoms linked to first and second aromatic rings, an azo group having a nitrogen atom linked to an aromatic ring, the aromatic ring having a hydroxy group, and two methoxy groups attached thereto. In preferred embodiments, the methoxy groups are both ortho to the hydroxy group.

In other embodiments the compound comprises an azo group having first and second nitrogen atoms linked to first and second aromatic rings, an azo group having a nitrogen atom linked to an aromatic ring, wherein the aromatic ring has a hydroxy group, a methyl group, and a methoxy group attached thereto. Preferably the methyl and methoxy groups are both ortho to the hydroxy group.

In some embodiments the biodegradable dye includes an azo group having first and second nitrogen atoms linked to first and second aromatic rings, an azo group having a nitrogen atom linked to an aromatic ring wherein the aromatic ring has a first substituent R1 selected from the group consisting of hydroxy and lower alkoxy, a second substituent $R_2$ selected from the group consisting of lower alkyl, lower alkoxy and fluorine, and a lower alkoxy substituent $R_3$. In preferred embodiments $R_1$ is hydroxy and $R_2$ is lower alkyl, with $R_2$ and $R_3$ both ortho to $R_1$.

In other embodiments the azo group has first and second nitrogen atoms linked to first and second aromatic rings, with the first aromatic ring having a hydroxy substituent para to the azo group, and a lower alkyl substituent ortho to the hydroxy substituent. In preferred embodiments, the lower alkyl substituent is methyl.

In another embodiment, the azo group has a nitrogen atom linked to an aromatic ring, with the ring having a first substituent $R_1$ and a second substituent $R_2$, wherein both $R_1$ and $R_2$ are lower alkoxy. Preferably, $R_1$ and $R_2$ are both methoxy. In other embodiments $R_1$ and $R_2$ are ortho to each other, or $R_1$ is para to the azo group.

In another embodiment, a plurality of azo groups have nitrogen atoms linked to first, second and third aromatic rings such that the compound of the fully conjugated system, wherein the first aromatic ring has a hydroxy and a lower alkoxy group attached thereto. The lower alkoxy group is preferably a methoxy.

In yet another embodiment, the azo group has first and second nitrogen atoms linked to first and second aromatic rings, wherein the first aromatic ring has a first substituent $R_1$ para to the nitrogen atom, wherein $R_1$ is selected from the group consisting of hydroxy and lower alkoxy, and a second substituent $R_2$ selected from the group consisting of methyl, ethyl and fluorine. In particular embodiments, $R_2$ is ortho to $R_1$. In yet other embodiments $R_2$ is methyl. In another embodiment the first aromatic ring has a third substituent $R_s$ selected from the group consisting of lower alkyl, lower alkoxy and a halogen, particularly wherein $R_3$ is ortho to $R_1$. In some specific embodiments, $R_2$ and $R_3$ are both methyl.

Several especially preferred embodiments are very completely degraded by Phanerochaete, and include 4-dimethylamino-azobenzene-4'-sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid.

Other compounds show some biodegradability when cultured with the Streptomyces strains of the present invention. Examples of such compounds having a higher degree of biodegradation with Streptomyces are the following: 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethyl-4-hydroxy-azobenzene-4'-sulfonic acid, 3,5-dimethoxy-4-hydroxy-azobenzene-4'-sulfonic acid, and 2-hydroxy-3-methoxy-5-methyl-azobenzene-4'-sulfonic acid and 4-diethylamino-azobenzene-4'-sulfonic acid.

Especially well degraded dyes with Streptomyces include 3-methyl-4-hydroxy-azobenzene-4'-sulfonic acid, 3-methoxy-4-hydroxy-azobenzene-4'-sulfonic acid, 3-sec-butyl-4-hydroxy-azobenzene-4'-sulfonic acid, 3,5-dimethyl-4-hydroxy-azobenzene-4'-sulfonic acid, 3,5-dimethoxy-4-hydroxy-azobenzene-4'-sulfonic acid. These dyes were significantly degraded by Streptomyces, that is degraded more than about 10%.

Particularly high Streptomyces degradation is observed when R1 is hydroxy, and R2 and R3 are methyl, particularly when the methyls are both ortho to the hydroxy. Similarly, high Streptomyces degradation is seen when R1 is hydroxy and R2 and R3 are both methoxy, particularly if both R2 and R3 are ortho to R1. Other Streptomyces degradable compounds include those in which R1 is hydroxy, R2 is methyl and R3 is methoxy, especially wherein R2 and R3 are both ortho to R1.

The present invention also includes a biodegradable composition containing an azo dye having a nitrogen atom linked to an aromatic ring with a lignin-like substitution pattern, wherein the composition also includes a microbe capable of degrading the dye. The ring has a first substituent $R_1$ selected from the group consisting of hydroxy, alkoxy and amino, and a second substituent $R_2$ selected from the group consisting of hydrogen, lower alkoxy, lower alkyl and hydrogen. The amino in preferred embodiments is secondary amine.

In particularly preferred embodiments of the composition, the microbe is *Phanerochaete chrysosporium*. Subspecies of the azo dye that are particularly useful in such a composition include those wherein R1 is hydroxy, particularly if R2 is a lower alkoxy, lower alkyl or halogen.

In yet other embodiments of the composition, the microbe is a Streptomyces, for example *S.rochei*, *S.chromofuscus*, *S.diastaticus*, *S.viridosporus*, or *S.badius*. Particularly useful strains of Streptomyces have been found to be *S.rochei* A10, A14, *S.chromofuscus* A11, A20, *S.diastaticus* A12, A13, *S.viridosporus* T7A and *S.badius* 252. Several compounds have been found to be particularly biodegradable in combination with Streptomyces. Such compounds include those in which R1 is hydroxy, particularly when R2 is ortho to the hydroxy. Enhanced biodegradability is also observed when the ring includes a third ring substituent R3 selected from the group consisting of lower alkyl and lower alkoxy. Biodegradability is particularly high when R1 is a hydroxy para to the azo linkage, and R2 is ortho to the hydroxy. In such embodiments, R2 is most preferably a lower alkoxy or lower alkyl.

In yet other embodiments of the invention, the biodegradability of xenobiotic dyes is increased by introducing a lignin-like aromatic ring into a preexisting azo dye.

Persons skilled in the art will recognize that azo dyes, other than those specifically disclosed, are included in the scope of this invention. Other microorganisms are also suitable for use in degrading these azo dyes. Soil microflora in general are a good source of additional microorganisms, which can be tested for biodegradative capacity as described in this specification. The dyes can also be degraded in soil itself, which contains many species of organisms capable of degrading the lignin-like dyes of the present invention.

The present application describes certain strains of soil Streptomyces species which are particularly effective at degrading the disclosed azo dyes. Such natural variability is expected, and is not evidence of any limitation of the method to use with particular strains of bacteria. Any person skilled in the art will be able to select bacteria from soil or elsewhere using the biotransformation assays disclosed herein. Actual selection of individual biodegradative species and strains is not essential because a mixture of soil microflora contains the microogranisms sufficient for azo dye biotransformation.

Table 2 illustrates that higher concentrations of azo dyes are sometimes less effectively degraded by *P.chrysosporium*. Dye 3, for example, becomes more toxic to the organism at 300 ppm, in contrast to concentrations below 300 ppm. Dyes 4 and 5 do not exhibit a similar degree of inhibition. In any case, toxic inhibition is not complete even at 300 ppm in sensitive organisms. Optimum concentrations of substrate are very specific to the substrate and organism of interest, and are subject to the kind of routine optimization known to those skilled in the art.

Having illustrated and described the principles of the invention in several preferred embodiments, it should be apparent to those skilled in the art that the invention can be modified in arrangement and detail without departing from such principles. We claim all modifications coming within the spirit and scope of the following claims.

We claim:

1. A biodegradable composition comprising:

an azo dye having first and second nitrogen atoms linked to first and second aromatic rings, the first ring having a first substituent $R_1$ selected from the group consisting of hydroxy, alkoxy and amino, and a second constituent $R_2$ selected from the group consisting of hydrogen, lower alkoxy, lower alkyl and halogen;

an amount of lignin peroxidase effective to degrade said dye, wherein lignin peroxidase is converted to lignin peroxidase II as the dye is degraded; and at least about 20 micromoles of veratryl alcohol, which amount is effective to recycle lignin peroxidase II to lignin peroxidase.

2. The composition of claim 1 wherein the lignin peroxidase is provided by a microbe.

3. The composition according to claim 1 having from about 20 micromoles to about 200 micromoles of veratryl alcohol.

4. The composition according to claim 1 wherein the first aromatic ring has a first substituent $R_1$ selected from the group consisting of hydroxy, lower alkoxy, or amino, and a second substituent $R_2$ selected from the group consisting of lower alkyl, lower alkoxy and halogen.

5. The composition of claim 4 wherein the azo dye further comprises a third ring substituent $R_3$ selected from the group consisting of lower alkyl, lower alkoxy, and halogen.

6. The composition of claim 1 wherein the azo dye further comprises a plurality of azo groups having nitrogen atoms linked to aromatic rings such that the compound is a fully conjugated system.

7. The composition according to claim 1 wherein the first aromatic ring has a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$.

8. A method of degrading xenobiotic azo dyes having first and second nitrogen atoms linked to first and second aromatic rings, the method comprising the steps of:

providing a first aromatic ring, wherein a first aromatic ring has a first substituent $R_1$ selected from the group consisting of hydroxy, alkoxy and amino, and a second substituent $R_2$ selected from the group consisting of hydrogen, lower alkoxy, lower alkyl and halogen; and exposing the mixture to an amount of lignin peroxidase effective to degrade the azo dye, wherein lignin peroxidase is converted to lignin peroxidase II as the dye is degraded.

9. The method according to claim 8 wherein the lignin peroxidase is provided by a microbe.

10. The method according to claim 8 and including the step of combining at least 20 micromoles of veratryl alcohol with the azo dye to form a mixture and exposing the mixture to lignin peroxidase, wherein the veratryl alcohol is added in an amount sufficient to convert lignin peroxidase II to lignin peroxidase.

11. The method according to claim 10 wherein from about 20 micromoles to about 200 micromoles of veratryl alcohol are combined with the azo dye.

12. The method according to claim 8 wherein the first aromatic ring has a first substituent $R_1$ selected from the group consisting of hydroxy, lower alkoxy, or amino, and a second substituent $R_2$ selected from the group consisting of lower alkyl, lower alkoxy and halogen.

13. The method according to claim 8 wherein the first aromatic ring has a first substituent $R_1$ selected from the group consisting of hydroxy, and lower alkoxy, a second substituent $R_2$ selected from the group consisting of lower alkyl, and lower alkoxy, and a third substituent $R_3$ selected from the group consisting of lower alkoxy and halogen.

14. A biodegradable composition comprising:

an azo dye having first and second nitrogen atoms linked to first and second aromatic rings, the first ring having a first substituent $R_1$ selected from the group consisting of hydroxy, methoxy, ethoxy, propoxy, butoxy and amino, and a second substituent $R_2$ selected from the group consisting of hydrogen, methyl, methoxy, ethyl, ethoxy, propyl, propoxy, butyl, butoxy and halogen;

an amount of lignin peroxidase effective to degrade said dye, wherein lignin peroxidase is converted to lignin peroxidase II as the dye is degraded; and at least about 20 micromoles of veratryl alcohol, which amount is effective to recycle lignin peroxidase II to lignin peroxidase.

15. A biodegradable composition comprising:

an azo dye having at least one azo group that includes first and second nitrogen atoms linked to first and second aromatic rings, the first aromatic ring having a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$;

an amount of lignin peroxidase effective to degrade said dye, wherein lignin peroxidase is converted to lignin peroxidase II as the dye is degraded; and at least about 20 micromoles of veratryl alcohol, which amount is effective to recycle lignin peroxidase II to lignin peroxidase.

16. A method of degrading xenobiotic azo dyes having at least one azo group that includes first and second nitrogen atoms linked to first and second aromatic rings, the method comprising the steps of:

providing an azo dye having at least one azo group that includes first and second nitrogen atoms linked to first and second aromatic rings, the first aromatic ring having a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$; and exposing the mixture to an amount of lignin peroxidase effective to degrade the azo dye, wherein lignin peroxidase is converted to lignin peroxidase II as the dye is degraded.

* * * * *